(12) United States Patent
LaBeaume et al.

(10) Patent No.: US 9,500,947 B2
(45) Date of Patent: *Nov. 22, 2016

(54) ACID GENERATOR COMPOUNDS AND PHOTORESISTS COMPRISING SAME

(71) Applicants: Rohm and Haas Electronic Materials LLC, Marlborough, MA (US); Dow Global Technologies LLC, Midland, MI (US)

(72) Inventors: Paul J. LaBeaume, Auburn, MA (US); Aaron A. Rachford, Midland, MI (US); Vipul Jain, North Grafton, MA (US)

(73) Assignees: Rohm and Haas Electronic Materials LLC, Marlborough, MA (US); Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/027,349

(22) Filed: Sep. 16, 2013

(65) Prior Publication Data

US 2014/0080059 A1    Mar. 20, 2014

Related U.S. Application Data

(60) Provisional application No. 61/701,591, filed on Sep. 15, 2012.

(51) Int. Cl.
```
G03F 7/004    (2006.01)
C07C 381/12   (2006.01)
G03F 7/20     (2006.01)
G03F 7/038    (2006.01)
G03F 7/039    (2006.01)
```

(52) U.S. Cl.
CPC ........... *G03F 7/0045* (2013.01); *C07C 381/12* (2013.01); *G03F 7/0046* (2013.01); *G03F 7/0382* (2013.01); *G03F 7/0392* (2013.01); *G03F 7/0397* (2013.01); *G03F 7/20* (2013.01)

(58) Field of Classification Search
CPC ...................... G03F 7/004; G03F 7/029; G03F 7/0382; G03F 7/0392; G03F 7/20; C07D 327/00; C07D 333/00; C07D 333/12; C07D 335/16; C07C 381/12
USPC ....... 430/270.1, 921, 922, 923, 924; 568/18; 549/27
See application file for complete search history.

(56) References Cited

U.S. PATENT DOCUMENTS

| | | | |
|---|---|---|---|
| 5,824,824 A | 10/1998 | Osawa et al. | |
| 7,615,330 B2 * | 11/2009 | Kamimura et al. | 430/270.1 |
| 7,776,510 B2 | 8/2010 | Iwai et al. | |
| 2001/0049071 A1 * | 12/2001 | Merritt et al. | 430/270.1 |
| 2002/0009668 A1 * | 1/2002 | Nishimura et al. | 430/270.1 |
| 2006/0194147 A1 * | 8/2006 | Kawanishi | 430/270.1 |
| 2007/0184384 A1 | 8/2007 | Kawanishi | |
| 2007/0224540 A1 | 9/2007 | Kamimura et al. | |
| 2009/0208872 A1 * | 8/2009 | Wolf et al. | 430/286.1 |
| 2010/0136478 A1 | 6/2010 | Kawaue et al. | |
| 2010/0239982 A1 * | 9/2010 | Choi et al. | 430/286.1 |
| 2010/0248149 A1 * | 9/2010 | Tsuchimura et al. | 430/296 |
| 2010/0297560 A1 | 11/2010 | Seshimo et al. | |
| 2010/0304296 A1 * | 12/2010 | Ichikawa et al. | 430/270.1 |
| 2014/0080060 A1 * | 3/2014 | LaBeaume | 430/281.1 |
| 2014/0080062 A1 * | 3/2014 | Thackeray et al. | 430/285.1 |
| 2014/0186767 A1 * | 7/2014 | Thackeray et al. | 430/281.1 |

FOREIGN PATENT DOCUMENTS

| | | |
|---|---|---|
| EP | 1906241 A1 | 2/2008 |
| JP | 2010044253 A | 2/2010 |
| WO | 03072567 A1 | 9/2003 |

OTHER PUBLICATIONS

English Summary of Taiwan Office Action of Taiwan Application No. 102133123 counterpart to present U.S. Appl. No. 14/027,375.
Selvaraju, C. et al. "Excited state reactions of acridinedione dyes with onium salts: mechanistic details", Journal of Photochemistry and Photobiology A: Chemistry vol. 138, Issue 3, Jan. 31, 2001, pp. 213-226, DOI: 10.1016/S1010-6030(00)00406-8, figure 1, table 4 and the last paragraph of right column of p. 223.

\* cited by examiner

*Primary Examiner* — Anca Eoff
(74) *Attorney, Agent, or Firm* — Mintz Levin Cohn Ferris Glovsky and Popeo, P.C.; Peter F. Corless

(57) ABSTRACT

Acid generator compounds are provided that are particularly useful as a photoresist composition component. Acid generator compounds of the invention comprise 1) a cyclic sulfonium salt and 2) a covalently linked photoacid-labile group. In one aspect, thioxanthone acid generator compounds are particularly preferred, including acid generator compounds that comprise (i) a thioxanthone moiety; and (ii) one or more covalently linked acid labile-groups.

29 Claims, No Drawings

ACID GENERATOR COMPOUNDS AND PHOTORESISTS COMPRISING SAME

This application claims the benefit of priority under 35 U.S.C. §119(e) to U.S. Provisional Application No. 61/701,591, filed Sep. 15, 2012, the entire contents of which application are incorporated herein by reference.

1. FIELD

The present invention relates to new acid generator compounds that comprise a cyclic sulfonium salt with a covalently linked acid-labile moiety and photoresist compositions that comprise such compounds.

2. INTRODUCTION

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating.

Known photoresists can provide features having resolution and dimension sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See US 20070224540 and EP 1906241. Extreme ultraviolet (EUV) and e-beam imaging technologies also have been employed. See U.S. Pat. No. 7,459,260. EUV utilizes short wavelength radiation, typically between 1 nm to 40 nm, with 13.5 nm radiation often employed.

EUV photoresist development continues to be a challenging issue for EUV Lithography (EUVL) technology implementation. Required are development of materials that can provide highly resolved fine features, including a low linewidth roughness (LWR), and sufficient sensitivity to afford wafer throughput.

SUMMARY

We have now discovered new acid generator compounds particularly useful as a photoresist composition component.

Acid generator compounds of the invention comprise 1) a cyclic sulfonium salt and 2) a covalently linked acid-labile group.

In preferred aspects, acid generator compounds and photoresists of the invention are particularly useful for EUV imaging. Preferred acid generators of the compound can exhibit favorable electrochemical reduction potentials (e.g., ≥−2.0 V vs. Ag/AgCl) and comparatively enhanced photospeeds upon exposure to EUV radiation.

In one aspect, thioxanthone acid generator compounds are particularly preferred, especially acid generator compounds that comprise (i) a thioxanthone moiety; and (ii) one or more covalently linked acid labile-groups.

In another preferred aspect, acid generator compounds of the invention may comprise a structure of Formula

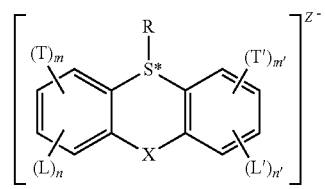

(I)

wherein: Z is a counter anion;
R is a non-hydrogen substituent;
X is >C=O; >S(O)$_2$; >S(O)$_2$; —C(=O)O—; —C(=O)NH—; —C(=O)—C(=O)—; —O—; CHOH; CH$_2$; or S;
each T and each T' are the same or different non-hydrogen substituent;
each L and each L' are the same or different acid-labile group, with T, L, T' and L' non-hydrogen groups may be taken together to form a ring;
m and m' are each independently 0 (where hydrogen would be present for the T or T'), 1, 2, 3 or 4; and n and n' are each independently 0 (where hydrogen would be present for the L or L'), 1, 2, 3 or 4, wherein if R does not comprise an acid-labile group, then at least one of n and n' is greater than zero whereby the acid generator compound comprises at least one acid-labile group. In certain aspects, preferably one or both of m and m' are 0.

In certain preferred aspects, an acid generator of the invention may be covalently linked to a polymer. Such polymer may be suitably utilized as a component of a photoresist composition. In such aspects, suitably the anion component but not the cation component of an ionic acid generator compound of the invention may be covalently linked to a polymer, or the cation component but not the anion component of the acid generator may be covalently linked to a polymer, or each of the anion and cation components of the acid generator may be covalently linked to a polymer.

As referred to herein, an acid-labile group of an acid generator compound when included in a photoresist composition will undergo a cleavage reaction during typical lithographic processing of the photoresist, i.e. upon exposure of a coating layer of the photoresist to activating radiation for the photoresist followed by any post-exposure thermal treatment of the pattern-wise exposed photoresist layer. Exemplary acid labile groups include acid-labile esters (e.g. t-butyl ester) and acetals.

In preferred aspects, acid generator compounds may comprise a cation component with covalently bound acid labile group, where the acid-labile group cleavage product comprises a relatively bulky moiety, e.g. a carboalicyclic (non-aromatic ring with all carbon ring atoms), heteroalicyclic (non-aromatic ring with one or more N, O or S ring atoms), aromatic groups such as optionally substituted phenyl, naphthyl and anthracrene. For example, preferred are such acid-labile groups that comprise an optionally substituted cyclopentyl, cyclohexyl, cycloheptyl, adamantyl, phenyl, napthyl or other group having from 5 to 20 or more ring atoms in a single or multi-ring structure.

Without being bound by theory, it is believed that use of such acid-labile groups can enhance lithographic performance of a photoresist comprising the acid generator compound, including by providing enhanced contrast relative to a comparable system that does not include such moieties.

As discussed, preferred acid generator compounds of the invention may exhibit an electrochemical reduction potential of ≥−2.0 V (vs. Ag/AgCl, cathodic peak potential) as determined by a standard electrochemical potential assay, such assay specifically defined below. In one aspect, particularly preferred acid generator compounds of the invention may exhibit an electrochemical reduction potential of at least −2.0 V to 0.0 V (vs. Ag/AgCl, cathodic peak potential), more preferably −0.9 to 0 V (vs. Ag/AgCl, cathodic peak potential), still more preferably −0.6 to −0.35 V (vs. Ag/AgCl, cathodic peak potential), as determined by a standard electrochemical potential assay, such assay specifically defined below.

Particularly preferred photoresists of the invention may comprise an imaging-effective amount of one or more acid generator compounds as disclosed herein and a suitable polymer component. Photoresists of the invention also may comprise a mixture of distinct acid generator compounds, typically a mixture of 2 or 3 different acid generator compounds, more typically a mixture that consists of a total of 2 distinct acid generator compounds.

Methods are also provided for forming relief images of photoresist compositions of the invention (including patterned lines with sub sub-50 nm or sub-20 nm dimensions). Substrates such as a microelectronic wafer also are provided having coated thereon a photoresist composition of the invention.

DETAILED DESCRIPTION

As referred to herein, acid generator compounds can produce an acid when exposed to activating radiation, such as EUV radiation, e-beam radiation or other radiation sources such as 193 nm wavelength radiation. Acid generator compounds as referred to herein also may be referred to as photoacid generator compounds.

Acid Generator Compounds

Particularly preferred acid generator compounds of the invention include compounds that comprise a structure of the following Formula (IA):

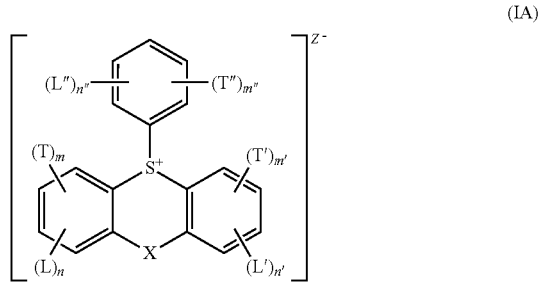

(IA)

wherein: Z is a counter anion;
X is >C=O; >S(O); >S(O)$_2$; —C(=O)O—; —C(=O)NH—; —C(=O)—C(=O)—; —O—; CHOH; CH$_2$; or S; each T, each T' and each T" are the same or different non-hydrogen substituent; each L, each L' and each L" are the same or different acid-labile group, with T, L, T', L', T" and L" non-hydrogen groups may be taken together to form a ring;
m and m' are each independently 0 (where hydrogen would be present for the T or T'), 1, 2, 3 or 4; m" is 0 (where hydrogen would be present for the T"), 1, 2, 3, 4 or 5; n and n' are each independently 0 (where hydrogen would be present for the L or L'), 1, 2, 3 or 4; n" is independently 0 (where hydrogen would be present for the L"), 1, 2, 3, 4 or 5; and at least one of n, n' and n" are other than 0. In certain aspects, preferably one or more of m, m' and m" are 0, and each of m, m' and m" may be 0.

Additional preferred acid generator compounds of the invention include compounds that comprise a structure of the following Formula (IB):

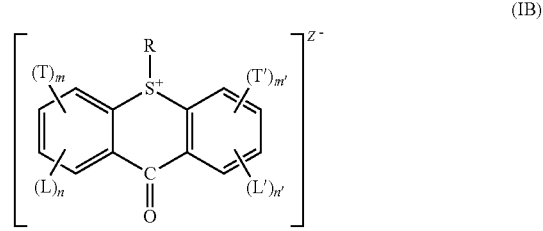

(IB)

wherein:
Z is a counter anion;
R is a non-hydrogen substituent;
each T and each T' are the same or different non-hydrogen substituent;
each L and each L' are the same or different acid-labile group, with T, L, T' and L' non-hydrogen groups may be taken together to form a ring;
m and m' are each independently 0 (where hydrogen would be present for the T or T'), 1, 2, 3 or 4; and n and n' are each independently 0 (where hydrogen would be present for the L or L'), 1, 2, 3 or 4. In certain aspects, preferably one or both of m and m' are 0. Preferably, a compound of Formula (IB) comprises an acid-labile group, e.g. R may comprise an acid-labile group and/or one or both of n and n' are greater than 0.

Particularly preferred acid generators of the invention include thioxanthone compounds that comprise a structure of the following Formula (IC):

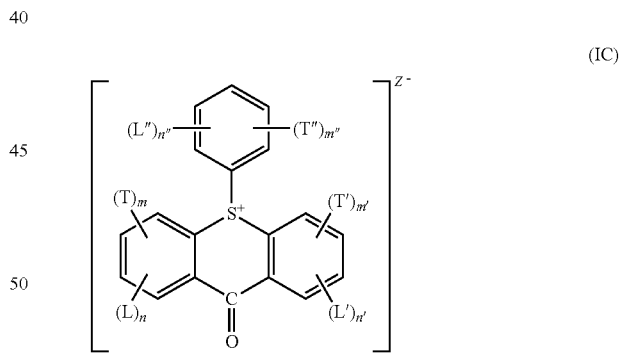

(IC)

wherein: Z is a counter anion;
each T, each T' and each T" are the same or different non-hydrogen substituent; each L, each L' and each L" are the same or different acid-labile group, with T, L, T', L', T" and L" non-hydrogen groups may be taken together to form a ring;
m and m' are each independently 0 (where hydrogen would be present for the T or T'), 1, 2, 3 or 4;
m" is 0 (where hydrogen would be present for the T"), 1, 2, 3, 4 or 5;
n and n' are each independently 0 (where hydrogen would be present for the L or L'), 1, 2, 3 or 4; n" is independently 0 (where the L" would be hydrogen), 1, 2, 3, 4 or 5; and at least one of n, n' and n" are other than 0. In certain aspects, preferably one or both of m and m' are 0.

As discussed above, suitable acid generators of the invention include thioxanthone compounds that comprise multi-cyclic fused ring systems which are substituents of the thioxanthone ring structure.

For instance, suitable are acid generators of the invention include structures of the following Formula (ID):

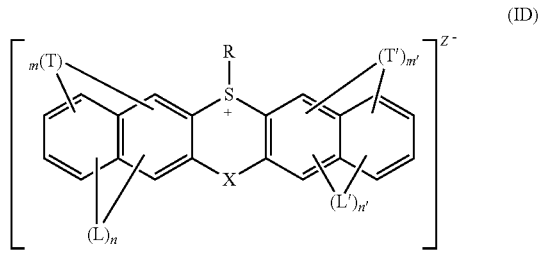

(ID)

wherein in Formulae (ID),

Z is a counter anion;

R is a non-hydrogen substituent;

X is >C=O; >S(O); >S(O)$_2$; —C(=O)O—; —C(=O)NH—; —C(=O)—C(=O)—; —O—; CHOH; CH$_2$; or S, and preferably X is >C=O;

each T and each T' are the same or different non-hydrogen substituent;

each L and each L' are the same or different acid-labile group;

m and m' are each independently 0 (where hydrogen would be present for the T or T'), 1 through 11;

n and n' are each independently 0 (where hydrogen would be present for the L or L'), 1 through 12, more typically 1 through 4, or even more typically 1, 2 or 3;

n" is independently 0 (where the L" would be hydrogen), 1, 2, 3, 4 or 5; and wherein if R does not comprise an acid-labile group, then at least one of n and n' is greater than zero whereby the acid generator compound comprises at least one acid-labile group. In certain aspects, preferably one or both of m and m' are 0.

Additional suitable are acid generators of the invention that comprise multi-cyclic fused ring systems which are substituents of a thioxanthone ring include structures of the following Formula (IE):

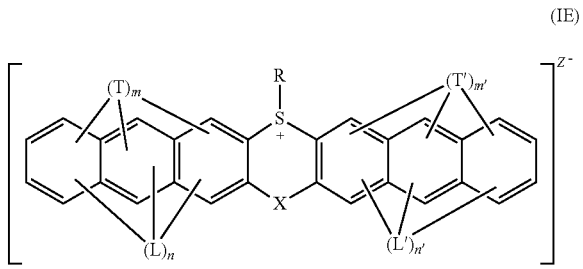

(IE)

wherein Formulae (IE)

Z is a counter anion;

R is a non-hydrogen substituent;

X is >C=O; >S(O); >S(O)$_2$; —C(=O)O—; —C(=O)NH—; —C(=O)—C(=O)—; —O—; CHOH; CH$_2$; or S, and preferably X is >C=O;

each T and each T' are the same or different non-hydrogen substituent;

each L and each L' are the same or different acid-labile group;

m and m' are each independently 0 (where hydrogen would be present for the T or T'), 1 through 15;

n and n' are each independently 0 (where hydrogen would be present for the L or L'), 1 through 16, more typically 1 through 4, or even more typically 1, 2 or 3; and wherein if R does not comprise an acid-labile group, then at least one of n and n' is greater than zero whereby the acid generator compound comprises at least one acid-labile group. In certain aspects, preferably one or both of m and m' are 0.

In the above Formulae (I), (IA), (TB), (IC), (ID) and (IE) suitable non-hydrogen substituents may be e.g. non-hydrogen substituent such as halo (F, Cl, Br or I), cyano, nitro, hydroxy, optionally substituted C$_{1-20}$alkyl, optionally substituted C$_{1-20}$alkoxy, such as optionally substituted alkyl (e.g. optionally substituted C$_{1-10}$ alkyl), optionally substituted alkenyl or alkynyl preferably having 2 to about 20 carbon atoms such as such as allyl; optionally substituted ketones preferably having 1 to about 20 carbon atoms; optionally substituted alkylthio preferably having 1 to about 20 carbon atoms; optionally substituted alkylsulfinyl preferably 1 to about 20 carbon atoms; optionally substituted alkylsulfonyl preferably having 1 to about 20 carbon atoms; optionally substituted carboxy preferably have 1 to about 20 carbon atoms (which includes groups such as —COOR' where R' is H or C$_{1-8}$alkyl, including esters that are substantially non-reactive with photoacid); optionally substituted alkaryl such as optionally substituted benzyl, optionally substituted carbocyclic aryl such as optionally substituted phenyl, naphthyl, acenaphthyl, or optionally substituted heteroalicyclic or heteroaromatic group such as pyridyl, furanyl, pyrrole, thiophene, furan, imidazole, pyrazole, oxazole, isoxazole, thiazole, isothiazole, triazole, furanzan, oxadiazole, thiadiazole, dithiazole, terazole, pyran, thiopyran, diazine, oxazine, thiazine, dioxine, dithine, and triazine and polyaromatic groups containing one or more of such moieties. Additionally, multiple substitients (e.g. two T or T' substituents present on adjacent carbons in any of the above formulae) may be taken together to form a ring such as a fused optionally substituted phenyl ring.

In the above Formulae (I), (IA), (ID), (IE), preferred X groups include >C=O; >S(O); >S(O)$_2$; —C(=O)O—; —C(=O)NH—; —C(=O)—C(=O)—; —O—; CHOH; or S; more preferably X may be C=O; >S(O); >S(O)$_2$; —C(=O)O—; —C(=O)NH—; —C(=O)—C(=O)—; —O—; or S; still more preferably X may be any one of C=O; >S(O); >S(O)$_2$; —C(=O)O—; or —C(=O)—C(=O)—.

In the above Formulae (I), (IA), (TB), (IC), (ID) and (IE) suitable acid-labile groups may be a variety of moieties, including photoacid-labile esters and acetals such as optionally substituted ethylcyclopentyl esters, methyladamantyl esters, ethyl adamantyl esters, t-butylesters, phenyl esters, naphthyl esters and others. Preferred acid labile groups of acid generators of the invention (including compounds of the above Formulae (I), (IA), (IB), (IC), (ID) and (IE)) may comprise acid-labile ester moieties such as a group of the formula —C(=O)O(CH$_2$)n(C=O)O-ALG, where n is an integer of from 1 to 12, preferably n is 1, 2, 3 or 4, and ALG is a group (e.g. that provides a quaternary carbon linked to the ester) that results in an acid labile moiety, such as t-butyl or a ring system with linking quaternary carbon such as 1-ethylcyclopenyl or methyladamantyl. Thus, in Formulae (I), (IA), (IB), (IC), (ID) and (IE), suitable R, L, L', L", L'" substituents may correspond to —C(=O)O(CH₂)n(C=O)O-ALG, where n is an integer of from 1 to 12, preferably n is 1, 2, 3 or 4, and ALG is a group (e.g. that provides a quaternary carbon linked to the ester) that results in an acid labile moiety, such as t-butyl or a ring system with linking quaternary carbon such as 1-ethylcyclopenyl or methyladamantyl.

In the above Formulae (I), (IA), (IB), (IC), (ID) and (IE), preferred acid-labile moieties may include groups that are linked through a phenolic (or other carboxylic aryloxy) linkage to fused ring structure, e.g. where any one L and/or L' in Formulae (I), (TB), (ID) or (IE), or any of L, L' and L" in Formulae (IA), (IC) are —OR where R is an acid labile group, such as an acid-labile group comprising an ether or ester moiety, e.g. a group of the formula —(C=O)OR³ where R³ is a non-hydrogen substituent that provide an acid labile group including where R³ is t-butyl, or more preferably a further ester linkage such as where R³ is —(CH₂)ₙ (C=O)O-ALG, where n is an integer of from 1 to 12, preferably n is 1, 2, 3 or 4, and ALG is a group (e.g. that provides a quaternary carbon linked to the ester) that results in an acid labile moiety, such as t-butyl or a ring system with linking quaternary carbon such as 1-ethylcyclopentyl or methyladamantyl.

In a particular aspect, acid generator compounds (including compounds of the above Formulae (I), (IA), (IB), (IC), (ID) and (IE)) are preferred that that comprise one or more acid-labile groups that comprise at least one ester linkage. Preferred acid-labile groups may comprise an ester linkage of the Formula (II):

—(C=O)OR³ (II)

wherein in Formula (II) R³ is a non-hydrogen substituent that provides an acid-labile moiety such as a carbamate, an acid-labile ester or acetal group. For instance, exemplary preferred R³ groups include t-butyl, or more preferably a further ester linkage such as where R³ is —(CH2)ₙ(C=O)O-ALG, where n is an integer of from 1 to 12, preferably n is 1, 2, 3 or 4, and ALG is a group (e.g. that provides a quaternary carbon linked to the ester) that results in an acid labile moiety, such as t-butyl or a ring system with linking quaternary carbon such as 1-ethylcyclopentyl or methyladamantyl.

In another particular aspect, acid generator compounds (including compounds of the above Formulae (I), (IA), (IB), (IC), (ID) and (IE)) are preferred that that comprise one or more acid-labile groups that comprise at least one ester linkage. Preferred acid-labile groups may comprise an ether linkage of the Formula (III):

—O(CXY)ₙR³ (III)

wherein in Formula (III) X and Y are independently hydrogen or a non-hydrogen substituent such as halogen (F, Cl, Br, I), C₁₋₁₀alkyl, C₁₋₁₀alkoxy; R³ is a non-hydrogen substituent that provides an acid-labile moiety such as a carbamate, an acid-labile ester or acetal group; and n is a positive integer such as any of 1 through 20, more typically n is any of 1-10 or 1-4. Exemplary preferred R³ groups include t-butyl, or more preferably a further ester linkage such as where R³ is —(CH2)ₙ(C=O)O-ALG, where n is an integer of from 1 to 12, preferably n is 1, 2, 3 or 4, and ALG is a group (e.g. that provides a quaternary carbon linked to the ester) that results in an acid labile moiety, such as t-butyl or a ring system with linking quaternary carbon such as 1-ethylcyclopentyl or methyladamantyl.

Such ester-containing acid-labile groups (such as those of Formula II) or ether-containing acid-labile groups (such as those of Formula III) can be a substituent at any various available positions of an acid generator compound. In certain preferred aspects, an ester-containing acid-labile group will be a ring substituent of a carbocyclic aryl group such as phenyl or multi-cyclic aromatic ring such as naphthyl or anthracenyl ring of an acid generator compound.

In certain aspects, an acid generator compound also may comprise multiple acid-labile groups, including multiple distinct acid-labile groups, including e.g. an acid generator compound that comprises at least one ester-containing acid-labile groups (such as those of Formula II) as well as at least one ether-containing acid-labile groups (such as those of Formula III).

As discussed above, in certain preferred aspects, an acid generator of the invention may be covalently bound to a polymer. The polymer suitably may be the primary matrix polymer of a photoresist (and comprise photoacid-labile groups in the case of a positive resist), or may be a further additive polymer to a resist. Suitable polymers comprising a covalently linked acid generator compound as disclosed herein may vary widely in molecular weight, e.g. suitable will be polymer that have weight average molecular weights of at least about 500, 1000, 2000, 5000, 10,000, or more.

As discussed, various moieties of acid generator compounds and other materials may be optionally substituted. A "substituted" substituent may be substituted at one or more available positions, typically 1, 2, or 3 positions by one or more suitable groups such as e.g. halogen (particularly F, Cl or Br); cyano; nitro; C₁₋₈ alkyl; C₁₋₈ alkoxy; C₁₋₈ alkylthio; C₁₋₈ alkylsulfonyl; C₂₋₈ alkenyl; C₂₋₈ alkynyl; hydroxyl; nitro; alkanoyl such as a C₁₋₆alkanoyl e.g. acyl, haloalkyl particularly C1-8 haloalkyl such as CF₃; —CONR where R is optionally substituted C₁₋₈alkyl; —COOH, COC, >C=O; and the like.

As discussed, preferred acid generator compounds of the invention may exhibit an electrochemical reduction potential of at least about −2.0 V (more preferably −0.9 to 0) as determined by a standard electrochemical potential assay (all vs. Ag/AgCl, cathodic peak potential), such assay defined to mean herein the following protocol: reduction potentials are cathodic peak potentials of irreversible voltammograms obtained in cyclic voltammetry experiments. Cyclic voltammograms are collected in a one compartment cell with a Pt working electrode (such as commercially available BASi, MF-2013), Pt wire auxiliary electrode (such as commercially available BASi, MW-4130), and Ag/AgCl reference electrode (such as commercially available BASi, MF-2052). All values are thus relative to the Ag/AgCl redox couple. A 0.1 M solution of tetrabutyl ammonium perchlorate (>99%) is dissolved into acetonitrile (HPLC grade) used as the electrolyte solution for all electrochemical experiments. Upon confirming a clean electrolyte solution, the acid generator compound is dissolved into the electrolyte solution (~10⁻³ M concentration for acid generator compound) followed by N₂ purging of the resulting solution for 5-10 minutes prior to electrochemical measurement. Three successive cyclic voltammograms are collected on each acid generator compound for determination of cathodic peak potentials. The scan rate for potential sweep suitably is 0.1 V/s with a step size of 0.01 V. No iR-compensation applied.

Acid generator compounds of the invention can be readily prepared. Exemplary preferred syntheses are set forth in the examples which follow. Thus, for instance, a reactive group (e.g. hydroxyl) of a cyclic sulfonium cation component can be reacted with a reactive group comprising a suitable acid-labile moiety (e.g. ester or acetal) to provide an acid generator compound of the invention with covalently linked acid-labile group. A suitable cation component can be prepared by reaction of 1) a compound with S-ring atom (e.g. thioxanthone, a substituted thioxathone such as 2-isopropyl-9H-thioxanthen-9-one, thioxanthone oxide, thianthrenoxide-5-ium, or phenoxathiine) compound with 2) reactive compound (e.g. an iodonium compound such as bis(4-tert-butylphenyl)iodonium). Suitable reagents with an S-ring atom are commercially available as well as described in the literature. See., e.g., *Org. Biomol. Chem.* 2006, 4, 4101. Acid generator compounds of the invention may comprise a variety of acid-labile groups, including both ester and acetal groups.

Specifically preferred acid generator compounds of the invention may comprise a cation component selected from the following:

10-(5-((2-(1-ethylcyclopentyloxy)-2-oxoethoxy)carbonyl)-2-methoxyphenyl)-9-oxo-4,4a,9,10-tetrahydrothioxanthylium;

10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium;

10-(4-tert-butylphenyl)-2-(2-(1-ethylcyclopentyloxy)-2-oxoethoxy)-1,3-dimethyl-9-oxo-9,10-dihydrothioxanthylium;

5-(5-((2-(1-ethylcyclopentyloxy)-2-oxoethoxy)carbonyl)-2-methoxyphenyl)-5H-thianthrenoxide-5-ium;

10-(4-tert-butylphenyl)-2-((2-(1-ethylcyclopentyloxy)-2-oxoethoxy)carbonyl)-9-oxo-9,10-dihydrothioxanthylium.

Additional specifically preferred cation components of acid generator compounds of the invention include the following:

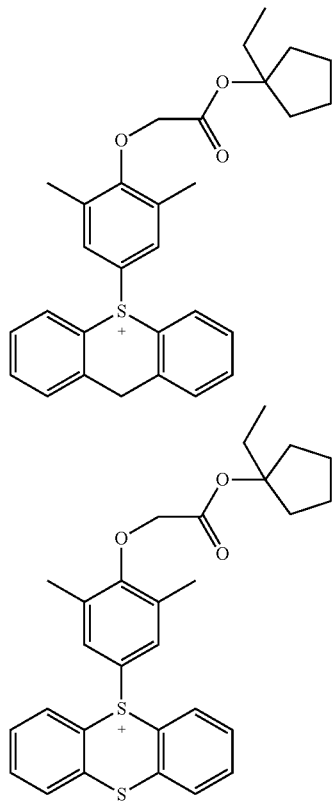

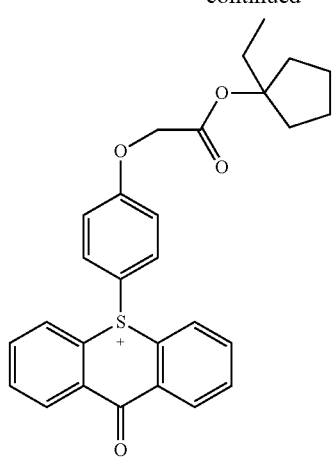

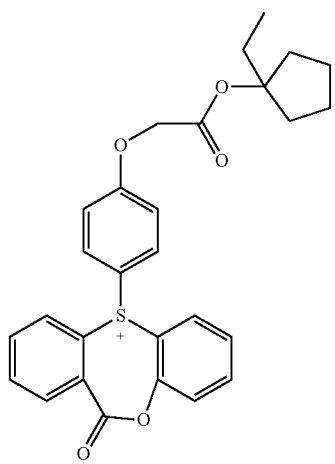

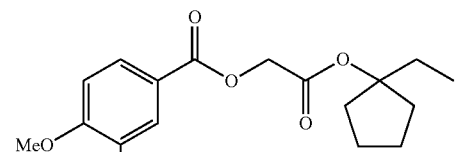

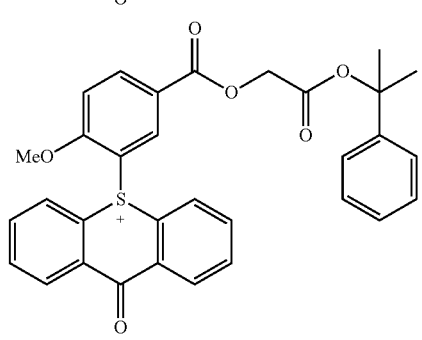

11
-continued
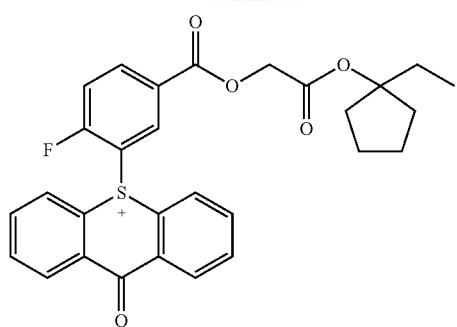
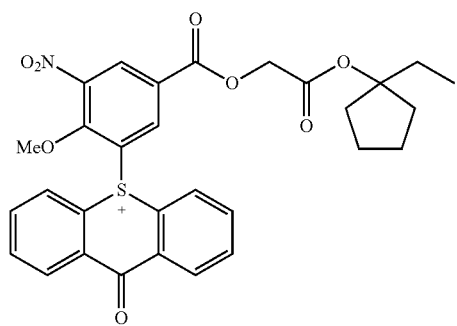
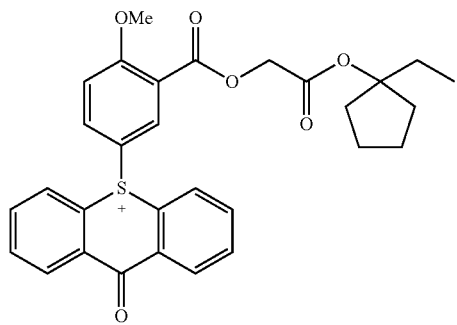
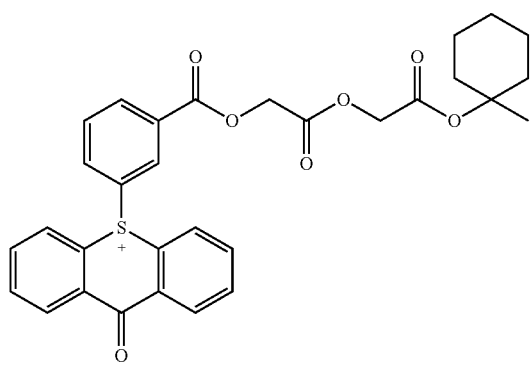
12
-continued
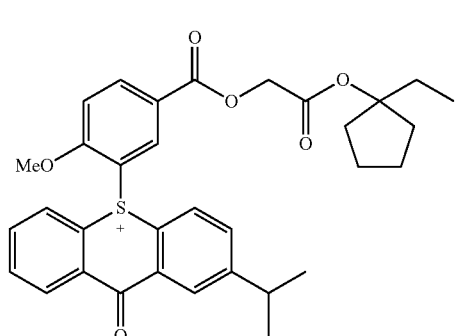
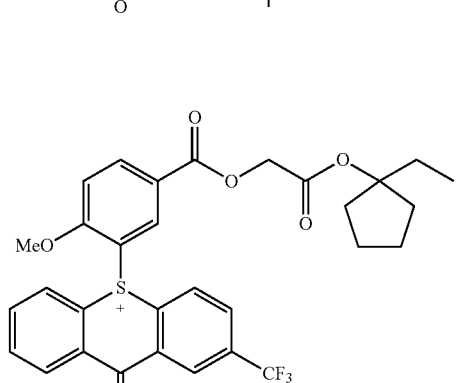
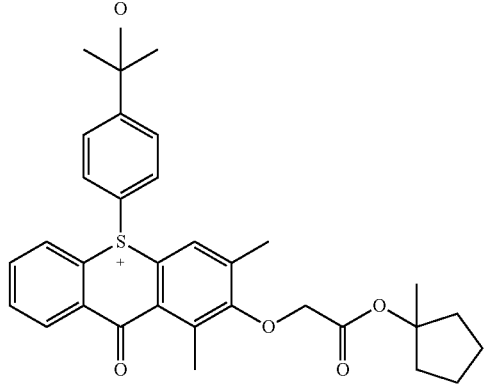

-continued

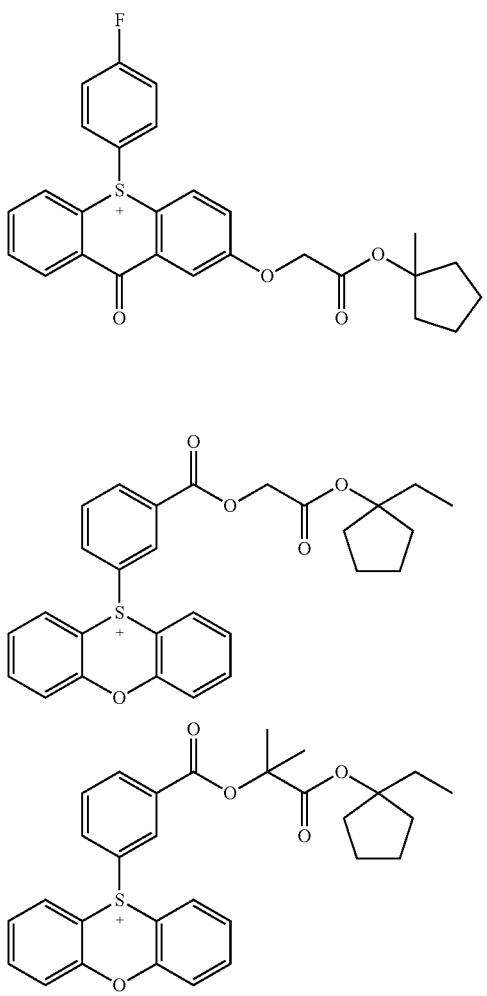

Specifically preferred anions of acid generator compounds of the invention include following:

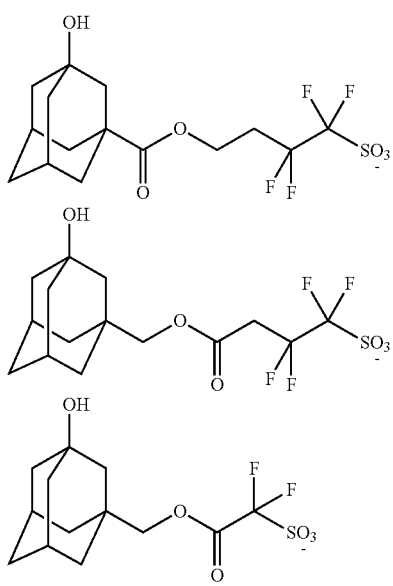

-continued

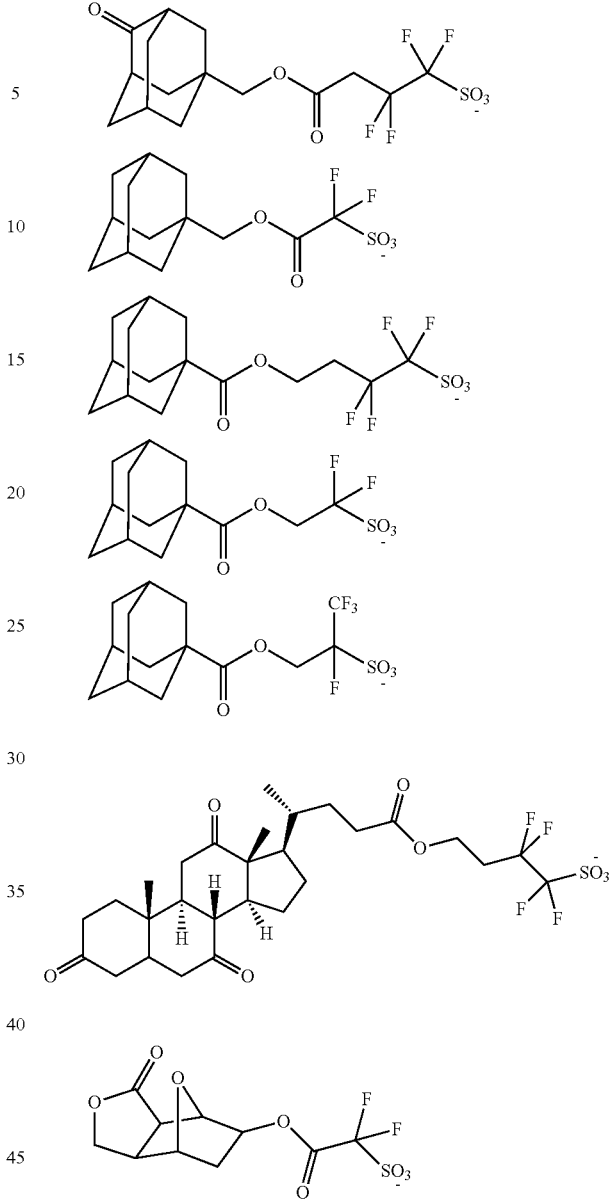

Photoresist Compositions

As discussed above, acid generator compounds as disclosed herein are useful as the radiation sensitive component in photoresist compositions, including both positive-acting and negative-acting chemically amplified resist compositions.

The photoresists of the invention typically comprise a polymer and one or more acid generator compounds as disclosed herein. Preferably the polymer has functional groups that impart alkaline aqueous developability to the resist composition. For example, preferred are polymers that comprise polar functional groups such as hydroxyl or carboxylate, or acid-labile groups that can liberate such polar moities upon lithographic processing. Preferably the polymer is used in a resist composition in an amount sufficient to render the resist developable with an aqueous alkaline solution.

Acid generator compounds of the invention are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation.

For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of acrylate or methacrylate monomers that comprise an acid-labile ester (e.g. t-butyl acrylate or methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-deprotectable monomer having the formula (V), a lactone-containing monomer of the formula (VI), a base-soluble monomer of formula (VII) for adjusting dissolution rate in alkaline developer, and an acid-generating monomer of the formula (VIII), or a combination comprising at least one of the foregoing monomers:

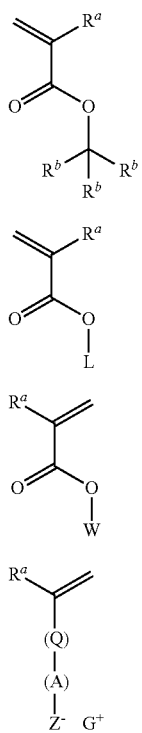

wherein each $R^a$ is independently H, F, —CN, $C_{1-10}$ alkyl, or $C_{1-10}$ fluoroalkyl. In the acid-deprotectable monomer of formula (V), $R^b$ is independently $C_{1-20}$ alkyl, $C_{3-20}$ cycloalkyl, $C_{6-20}$ aryl, or $C_{7-20}$ aralkyl, and each $R^b$ is separate or at least one $R^b$ is bonded to an adjacent $R^b$ to form a cyclic structure. In lactone-containing monomer of formula (VI), L is a monocyclic, polycyclic, or fused polycyclic $C_{4-20}$ lactone-containing group. In the base solubilizing monomer of formula (VII), W is a halogenated or non-halogenated, aromatic or non-aromatic $C_{2-50}$ hydroxyl-containing organic group having a pKa of less than or equal to 12. In the acid generating monomer of formula (VIII), Q is ester-containing or non-ester containing and fluorinated or non-fluorinated and is $C_{1-20}$ alkyl, $C_{3-20}$ cycloalkyl, $C_{6-20}$ aryl, or $C_{7-20}$ aralkyl group, A is ester-containing or non-ester-containing and fluorinated or non-fluorinated, and is $C_{1-20}$ alkyl, $C_{3-20}$ cycloalkyl, $C_{6-20}$ aryl, or $C_{7-20}$ aralkyl, $Z^-$ is an anionic moiety comprising carboxylate, sulfonate, an anion of a sulfonamide, or an anion of a sulfonimide, and $G^+$ is a sulfonium or iodonium cation.

Exemplary acid-deprotectable monomers include but are not limited to:

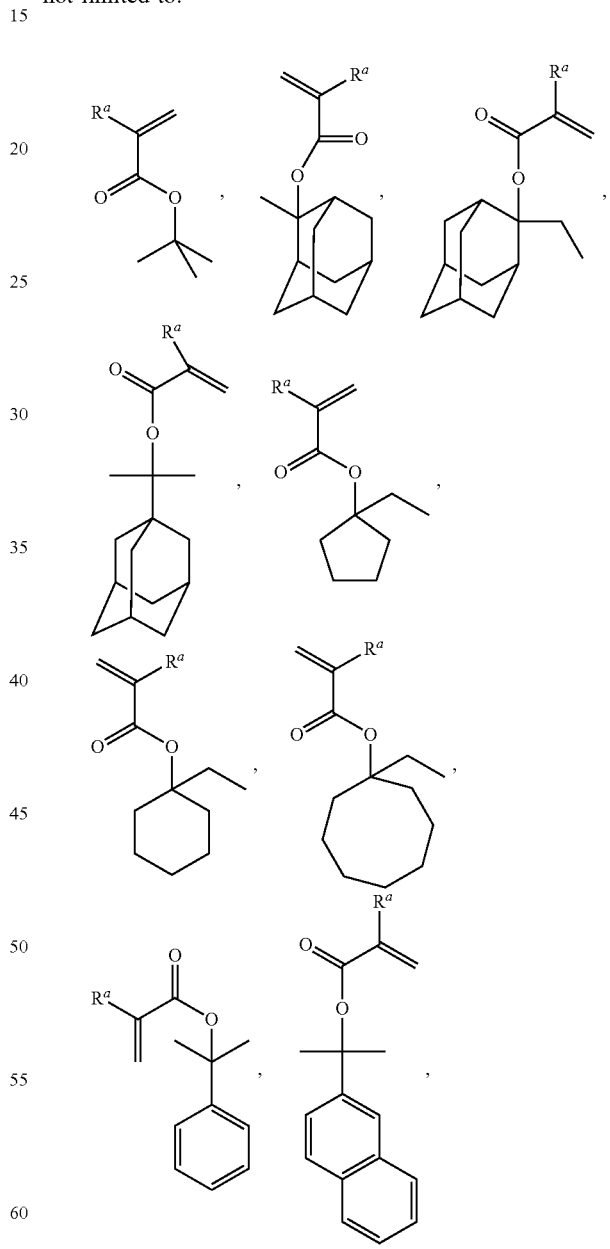

or a combination comprising at least one of the foregoing, wherein $R^a$ is H, F, —CN, $C_{1-6}$ alkyl, or $C_{1-6}$ fluoroalkyl.

Suitable lactone monomers may be of the following formula (IX):

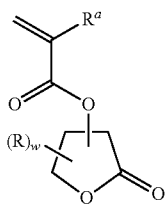
(IX)

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (IX), R is attached directly to the lactone ring or commonly attached to the lactone ring and/or one or more R groups, and the ester moiety is attached to the lactone ring directly, or indirectly through R.

Exemplary lactone-containing monomers include:

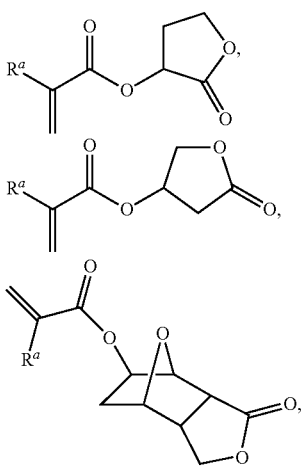

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (X):

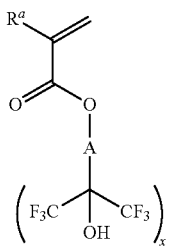
(X)

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non-fluorinated $C_{1-20}$ alkylene, $C_{3-20}$ cycloalkylene, $C_{6-20}$ arylene, or $C_{7-20}$ aralkylene, and x is an integer of from 0 to 4, wherein when x is 0, A is a hydroxyl-containing $C_{6-20}$ arylene.

Exemplary base soluble monomers include those having the following structures:

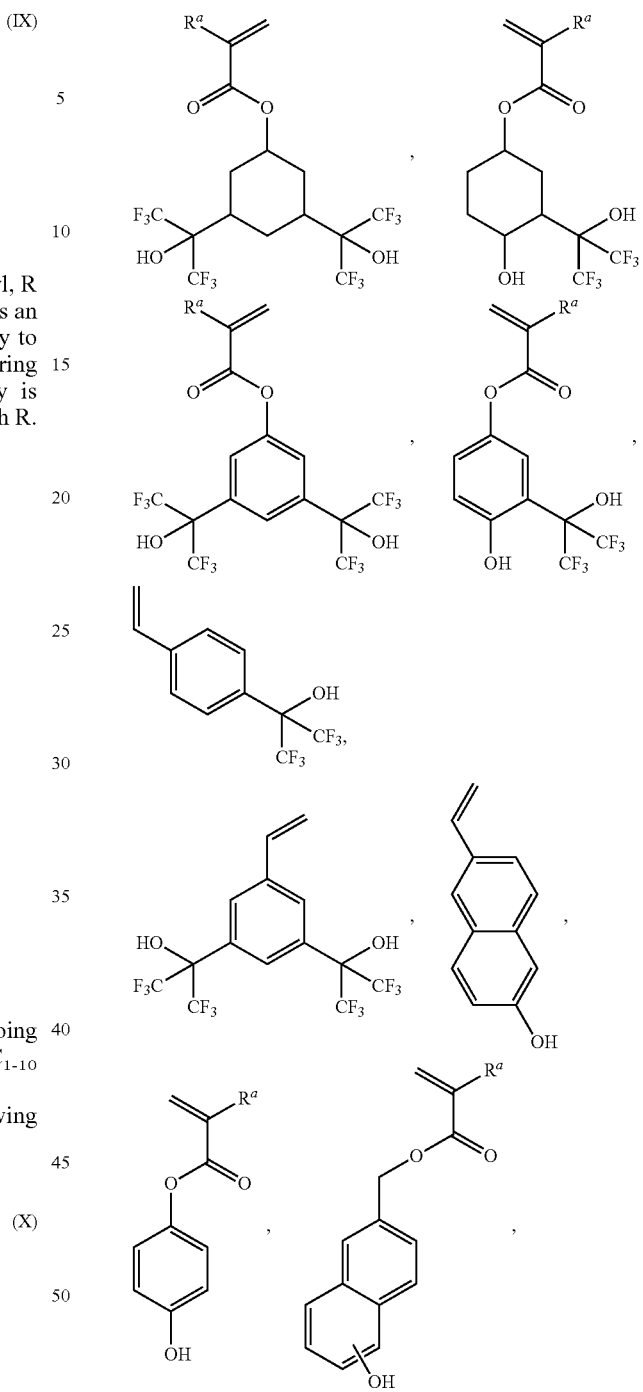

or a combination comprising at least one of the foregoing, wherein $R^a$ is H, F, —CN, $C_{1-6}$ alkyl, or $C_{1-6}$ fluoroalkyl.

Preferred acid generating monomers include those of the formulae (XI) or (XII):

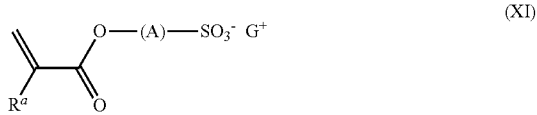
(XI)

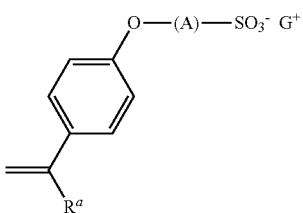

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XI) and (XII), A is a $\lceil (C(R^1)_2)_x C(=O)O]_b$—$C((R^2)_2)_y(CF_2)_z$— group, or an o-, m- or p-substituted —$C_6F_4$-group, where each $R^1$ and $R^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred acid generating monomers include:

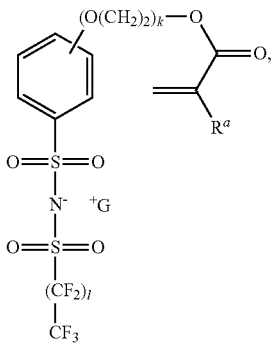

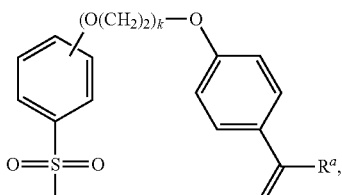

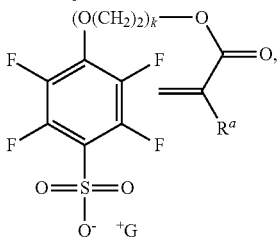

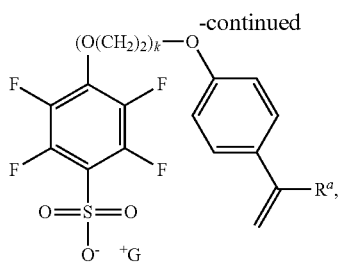

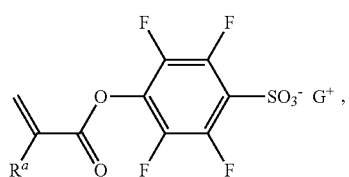 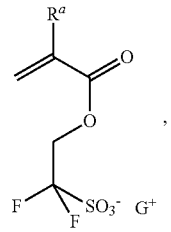

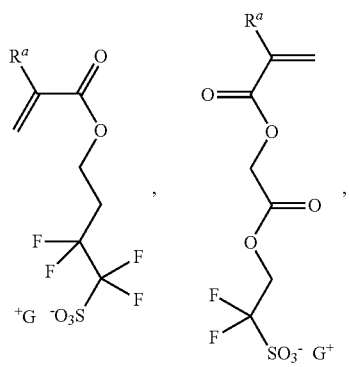

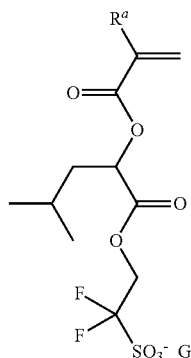

or a combination comprising at least one of the foregoing, where each $R^a$ is independently H, F, —CN, $C_{1-6}$ alkyl, or $C_{1-6}$ fluoroalkyl, k is an integer of 0 to 5; and $G^+$ is a sulfonium or iodonium cation.

Preferred acid-generating monomers may include sulfonium or iodonium cation. Preferably, in formula (IV), $G^+$ is of the formula (XIII):

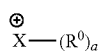

(XIII)

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^0$ groups is optionally attached to one adjacent $R^0$ group by a single bond, and a is 2 or 3, wherein when X is I, a is 2, or when X is S, a is 3.

Exemplary acid generating monomers include those having the formulas:

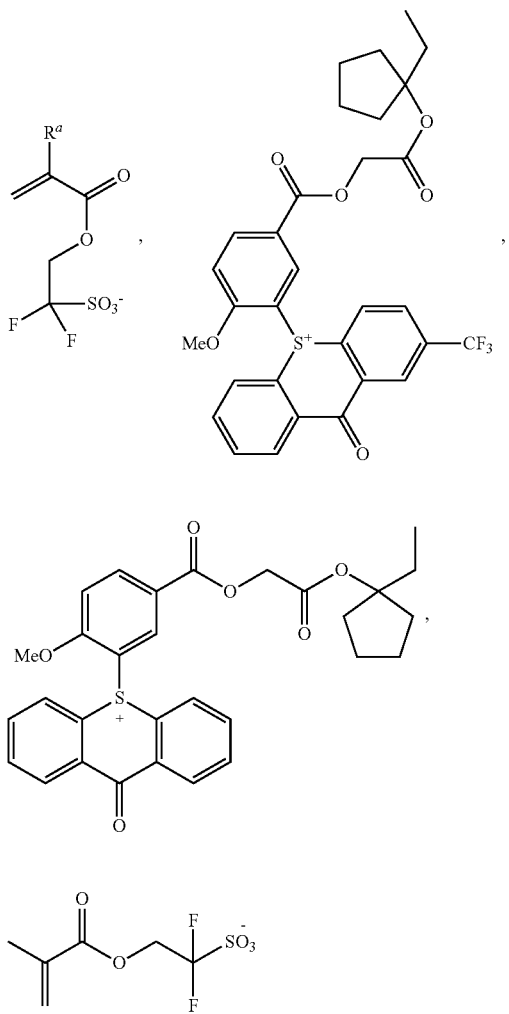

wherein $R^a$ is H, F, —CN, $C_{1-6}$ alkyl, or $C_{1-6}$ fluoroalkyl.

Specifically suitable polymers that have acid-labile deblocking groups for use in a positive-acting chemically-amplified photoresist of the invention have been disclosed in European Patent Application 0829766A2 (polymers with acetal and ketal groups) and European Patent Application EP0783136A2 (terpolymers and other copolymers including units of 1) styrene; 2) hydroxystyrene; and 3) acid labile groups, particularly alkyl acrylate acid labile groups.

Polymers for use in photoresists of the invention may suitably vary widely in molecular weight and polydisperity. Suitable polymers include those that have a $M_w$ of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and a photoactive component of the invention. Preferred negative acting compositions comprise a polymer binder such as a phenolic or non-aromatic polymer, a crosslinker component and a photoactive component of the invention. Such compositions and the use thereof have been disclosed in EP Patent Appl 0164248 and U.S. Pat. No. 5,128,232. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

Photoresists of the invention also may contain other materials. For example, other optional additives include actinic and contrast dyes, anti-striation agents, plasticizers, speed enhancers, sensitizers, photodestroyable bases etc. Such optional additives typically will be present in minor concentration in a photoresist composition.

Inclusion of base materials, preferably the carboxylate or sulfonate salts of photo-decomposable cations, provides a mechanism for neutralization of acid from the acid decomposable groups, and limits the diffusion of the photogenerated acid, to thereby provide improved contrast in the photoresist.

Photo-destroyable bases include photo-decomposable cations, and preferably those also useful for preparing PAGs, paired with an anion of a weak (pKa>2) acid such as, for example, a $C_{1-20}$ carboxylic acid. Exemplary such carboxylic acids include formic acid, acetic acid, propionic acid, tartaric acid, succinic acid, cyclohexylcarboxylic acid, benzoic acid, salicylic acid, and other such carboxylic acids.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, 1,1′,1″,1‴-(ethane-1,2-diylbis(azanetriyl))tetrapropan-2-ol; aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), or ionic quenchers including quaternary alkyl ammonium salts such as tetrabutylammonium hydroxide (TBAH) or tetrabutyl ammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Such photoresists may include the copolymer in an amount of 50 to 99 wt %, specifically 55 to 95 wt %, more specifically 60 to 90 wt %, and still more specifically 65 to 90 based on the total weight of solids. The photo-destroyable base may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, specifically less than or equal to 20%, or more specifically less than or equal to 10%, based on the total weight of solids. The total solids content for the photoresist composition may be 0.5 to 50 wt %, specifically 1 to 45 wt %, more specifically 2 to 40 wt %, and still more specifically 5 to 30 wt %, based on the total weight of solids and solvent. The acid generator compound(s) should be present in an amount sufficient to enable generation of a latent image in a coating layer of the resist. More specifically, the one or more acid generator compounds will suitably be present in an amount of from about 1 to 50 weight percent of total solids of a resist. It will be understood that the solids includes copolymer, photo-destroyable base, quencher, surfactant, any added PAG, and any optional additives, exclusive of solvent.

A coated substrate may be formed from the photoresist containing acid generator compound(s) which should be present in an amount sufficient to enable generation of a latent image in a coating layer of the resist. Such a coated substrate includes: (a) a substrate having one or more layers to be patterned on a surface thereof; and (b) a layer of the photoresist composition including the polymer-bound PAG over the one or more layers to be patterned. For EUV or e beam imaging, photoresists may suitably have relatively higher content of acid generator compound(s), e.g. where the one or more acid generator compounds comprise 5 to 10 to about 65 weight percent of total solids of the resist. Typically, lesser amounts of the photoactive component will be suitable for chemically amplified resists.

The photoresists of the invention are generally prepared following known procedures with the exception that one or more acid generator compounds of the invention are substituted for prior photoactive compounds used in the formulation of such photoresists. The photoresists of the invention can be used in accordance with known procedures.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

Additionally, for positive resists, unexposed regions can be selectively removed by treatment with a suitable nonpolar solvent for negative tone development. See U.S. 2011/0294069 for suitable procedures for negative tone development of positive photoresists. Typical nonpolar solvents for negative tone development are organic developers, such as a solvent chosen from ketones, esters, hydrocarbons, and mixtures thereof, e.g. acetone, 2-hexanone, methyl acetate, butyl acetate, and terahydrofuran.

The photoresist may, when used in one or more such a pattern-forming processes, be used to fabricate electronic and optoelectronic devices such as memory devices, processor chips (CPU's), graphics chips, and other such devices.

EXAMPLES 1-21

Syntheses of Acid Generator Compounds

Example 1

Synthesis of 2-(trifluoromethyl)-9H-thioxanthen-9-one oxide

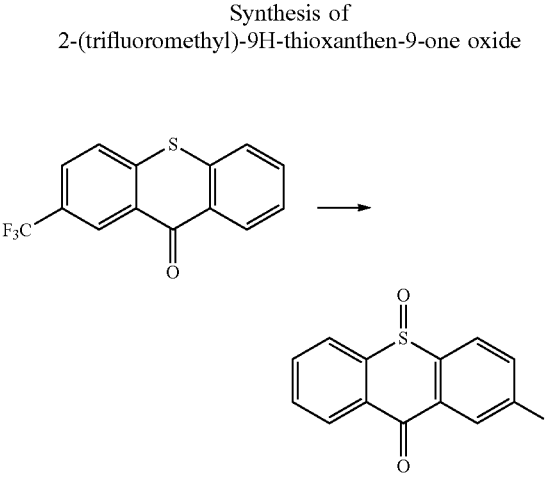

Hydrogen peroxide (4.68 g, 130 mmol) followed by chlorotrimethylsilane (8.24 mL, 64.9 mmol) were added to a solution of 2-(trifluoromethyl)-9H-thioxanthen-9-one (18.2 g, 64.9 mmol) in dioxane (200 mL) and stirred at room temperature until the starting material was consumed via TLC analysis. The reaction mixture was diluted with water (700 mL), filtered and dried to afford the title compound (quantitative yield @ 60% purity) as a white solid. NMR (300 MHz, $(CD_3)_2CO$) δ: 8.46-8.50 (m, 1H), 8.31-8.40 (m, 3H), 8.18 (d, J=8 Hz, 1H), 8.03 (t, J=8 Hz, 1H), 7.89 (t, J=8 Hz, 1H).

Example 2

Synthesis of Thioxanthone Oxide

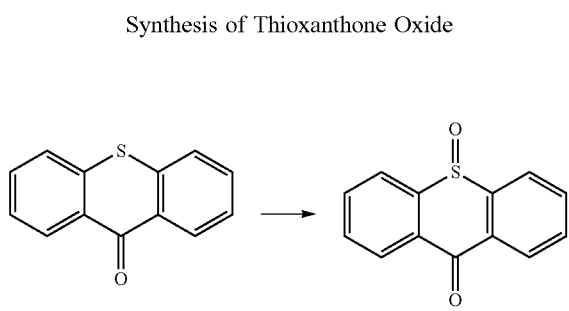

Hydrogen peroxide (53.4 g, 471 mmol) followed by chlorotrimethylsilane (29.9 mL, 236 mmol) were added to a solution of thioxanthone (18.2 g, 64.9 mmol) in dioxane (1 L) and stirred at room temperature until the starting material was consumed via TLC analysis. The reaction mixture was diluted with water (3 L), filtered and dried to afford the title compound (quantitative yield @ 80% purity) as a white solid. NMR (300 MHz, $(CD_3)_2CO$) δ: 8.35 (d, J=7.8 Hz, 2H), 8.17 (d, J=7.8 Hz, 2H), 8.01 (t, J=7.8 Hz, 2H), 7.86 (d, J=7.8 Hz, 2H).

Example 3

Synthesis of ethoxymethyl 4-methoxybenzoate

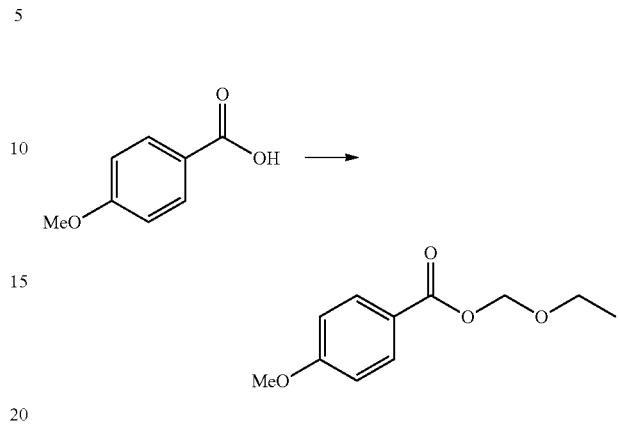

DIPEA (37.2 mL, 214 mmol) was added to a solution of chloromethyl ethyl ether (20.2 g, 213.6 mmol) and 4-methoxybenzoic acid (25.0 g, 164 mmol) in dichloromethane (400 mL) at 0° C. and stirred for 1 h. The reaction mixture was washed with 1% HCl (500 mL), 1% $NaHCO_3$ (500 mL), water (3×500 mL), dried ($Na_2SO_4$) and concentrated to afford the title compound (33.2 g, 96%) as a white wax. NMR (300 MHz, $(CD_3)_2CO$) δ: 8.01 (d, J=9 Hz, 2H), 7.05 (d, J=9 Hz, 2H), 5.49 (s, 2H), 3.90 (s, 3H), 3.76 (q, J=6.8 Hz, 2H), 1.20 (t, J=6.9 Hz, 3H).

Example 4

Synthesis of 1-ethylcyclopentyl 2-bromoacetate

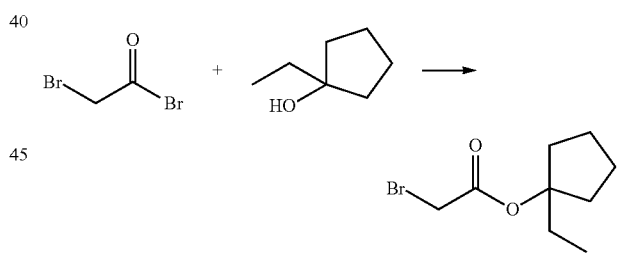

Pyridine (67.5 g, 0.854 mol) was added dropwise to a solution of ethylcyclopropanol (75.0 g, 675 mmol) in anhydrous dichloromethane (750 mL) under $N_2$ at 0° C. and stirred for 5 minutes. Bromoacetyl bromide (172 g, 74.4 mL, 854 mmol) in dichloromethane (75 mL) was added dropwise and the solution stirred at 0° C. for 20 h. The pyridinium bromide was filtered off, washed with $CH_2(Cl_2)$ (2×300 mL) and the solid pyridinium bromide discarded. The combined organic layers were washed with water (4×750 mL), and concentrated in vacuo. The crude oil was purified via of silica gel flash column chromatography (neutralized with TEA, 1:0 to 99:1 heptane:ethyl acetate). After concentration, the oil was filtered to afford the title compound (130 g, 84%) as a light orange oil. NMR (500 MHz, $(CD_3)_2SO$) δ: 3.93 (s, 2H), 2.07-2.14 (m, 2H), 2.00 (q, J=7 Hz, 2H), 1.59-1.77 (m, 4H), 0.89 (t, J=7 Hz, 3H).

Example 5

Synthesis of 10-(5-carboxy-2-methoxyphenyl)-9-oxo-9,10-dihydrothioxanthylium trifluoromethanesulfonate

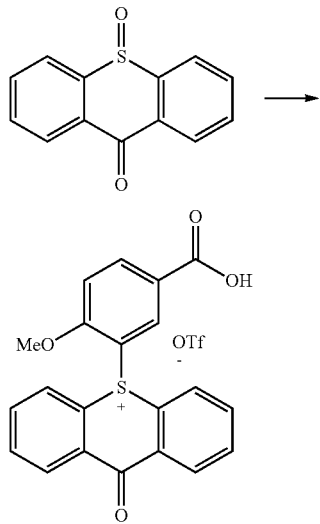

Triflic anhydride (81.2 g, 288 mmol) was added to a solution of thioxanthone oxide (33 g, 144 mmol) and ethoxymethyl 4-methoxybenzoate (30.3 g, 144 mmol) in dichloromethane (400 mL) at −78° C. and slowly warmed to 0° C. The reaction mixture was quenched with water (500 mL), stirred overnight and filtered. The solid was refluxed in MTBE (500 mL) and filtered to afford the title compound (20.0 g, 27% (not optimized)) as an off white solid. NMR (300 MHz, $(CD_3)_2CO$) δ: 13.0-13.4 (brs, 1 COOH), 8.53 (d, J=8 Hz, 2H), 8.34 (d, J=8 Hz, 2H), 8.21 (dd, J=8, 1.5 Hz, 1H), 7.98 (t, J=8 Hz, 2H), 7.79 (t, J=8 Hz, 2H), 7.51 (d, J=8 Hz, 1H), 7.45 (vis s, 1H).

Example 6

10-(5-((2-(1-ethylcyclopentyloxy)-2-oxoethoxy)carbonyl)-2-methoxyphenyl)-9-oxo-4,4a,9,10-tetrahydrothioxanthylium

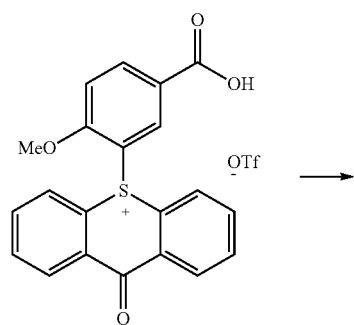

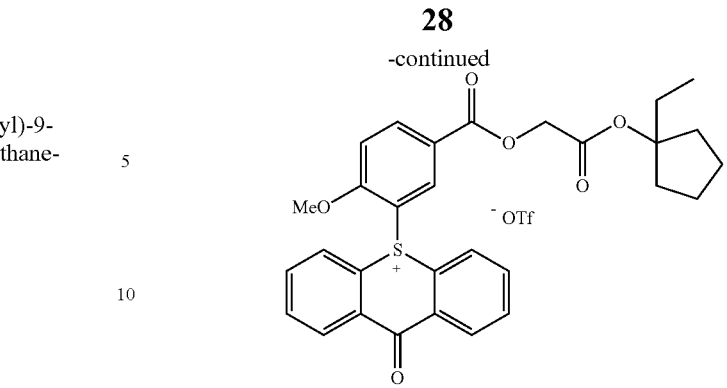

1-ethylcyclopentyl 2-bromoacetate (9.29 g, 39.5 mmol) was added to a solution of 10-(5-carboxy-2-methoxyphenyl)-9-oxo-4,4a,9,10-tetrahydrothioxanthylium trifluoromethanesulfonate (18.5 g, 35.9 mmol) and cesium carbonate (16.4 g, 50.3 mmol) in DMF (100 mL) at 0° C. and warmed to r.t. overnight. The reaction mixture was diluted with water (500 mL), extracted with dichloromethane (4×300 mL) and the combined organics washed with dilute HCl (400 mL) then water (2×400 mL). The combined aqueous layers were back extracted with dichloromethane (2×250 mL) and the combined organic layers dried ($Na_2SO_4$), concentrated to c.a. 50 mL and poured onto MTBE/heptane under vigerous stirring. The solid was filtered, washed with MTBE (2×250 mL) and dried in vacuo to afford the title compound (20.9 g, 87%) as an off white solid. NMR (300 MHz, $(CD_3)_2SO$) δ: 9.04 (d, J=2.4 Hz, 1H), 8.51-8.57 (m, 2H), 8.38 (dd, J=6.9, 2.4 Hz, 1H), 8.21-8.25 (m, 2H), 7.93-8.04 (m, 4H), 7.34 (d, J=6.9 Hz, 1H), 4.91 (s, 2H), 3.47 (s, 3H), 1.90-2.09 (m, 4H), 1.52-1.73 (m, 6H), 0.88 (t, J=7.2 Hz, 3H).

Example 7

Synthesis of 10-(5-((2-(1-ethylcyclopentyloxy)-2-oxoethoxy)carbonyl)-2-methoxyphenyl)-9-oxo-4,4a,9,10-tetrahydrothioxanthylium iodide

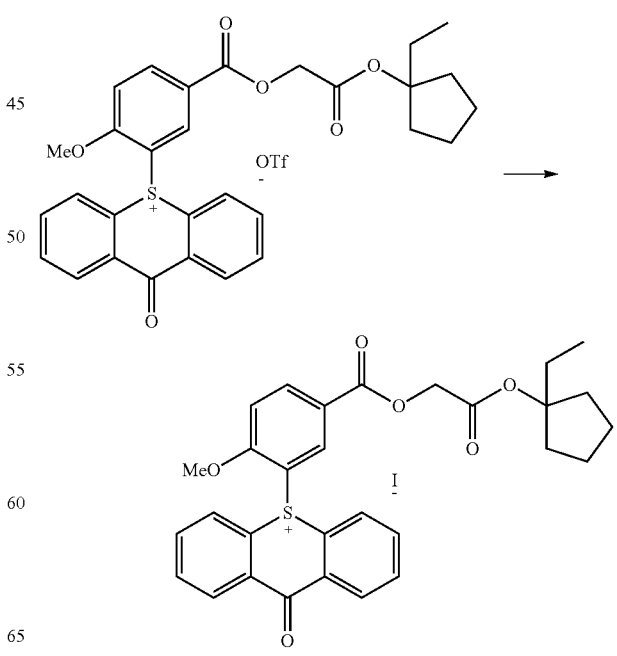

10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium trifluoromethanesulfonate (20.9 g, 31.3 mmol) was dissolved in dichloromethane (250 mL), washed with 1M aqueous sodium iodide (4×250 mL), water (4×250 mL), dried ($Na_2SO_4$) and concentrated to afford the title compound (17.1 g, 84%) as a light orange solid. NMR (300 MHz, $(CD_3)_2SO$) δ: 9.05 (vis s, 1H), 8.52-8.59 (m, 2H), 8.35-8.43 (m, 1H), 8.20-8.28 (m, 2H), 7.93-8.08 (m, 4H), 7.35 (d, J=10 Hz, 1H), 4.91 (s, 2H), 3.47 (s, 3H), 1.90-2.10 (m, 4H), 1.5-1.73 (m, 6H), 0.89 (t, J=7 Hz, 3H).

Example 8

Synthesis of 10-(5-((2-(1-ethylcyclopentyloxy)-2-oxoethoxy)carbonyl)-2-methoxyphenyl)-9-oxo-4,4a,9,10-tetrahydrothioxanthylium 1,1-difluoro-2-(methacryloyloxy)ethanesulfonate

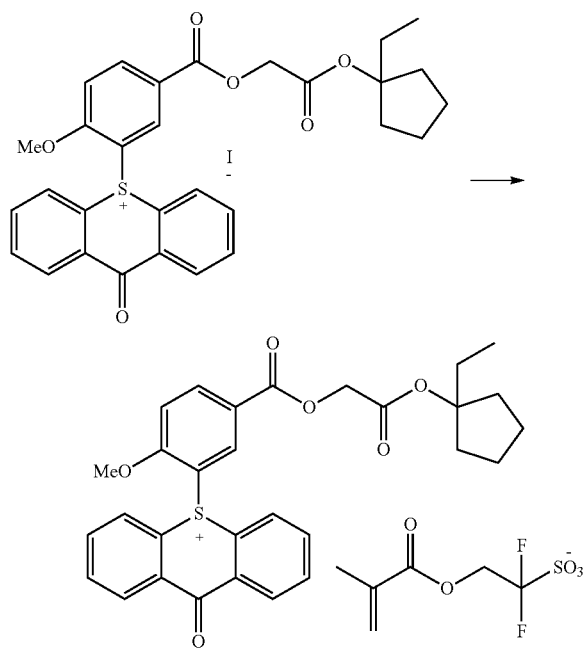

10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium iodide (5.00 g, 7.73 mmol) and triethylammonium 1,1-difluoro-2-(methacryloyloxy)ethanesulfonate (2.69 g, 8.12 mmol) were dissolved in dichloromethane (125 mL) and water (125 mL) and stirred at r.t. overnight. The layers were separated and the aqueous phase washed with dichloromethane (3×100 mL). The combined organic layers were washed with water (4×250 mL) and concentrated to afford the title compound (5.56 g, 96%) as a light orange solid. NMR (300 MHz, $(CD_3)_2SO$) δ: 9.04 (vis s, 1H), 8.51-8.58 (m, 2H), 8.39 (dd, J=10, 2.4 Hz, 1H), 8.21-8.27 (m, 2H), 7.95-8.05 (m, 4H), 7.35 (d, J=10 Hz, 1H), 6.09-6.12 (m, 1H), 5.76-5.78 (m, 1H), 4.91 (s, 1H), 4.62 (dd, J=16.2, 1.2 Hz, 2H), 3.47 (s, 3H), 1.88-2.09 (m, 7H), 1.52-1.73 (m, 6H), 0.89 (t, J=7.5 Hz, 3H).

Example 9

Synthesis of 10-(5-((2-(1-ethylcyclopentyloxy)-2-oxoethoxy)carbonyl)-2-methoxyphenyl)-9-oxo-4,4a,9,10-tetrahydrothioxanthylium 3-hydroxyadamantane-acetoxy-1,1,2,2-tetrafluorobutane-1-sulfonate

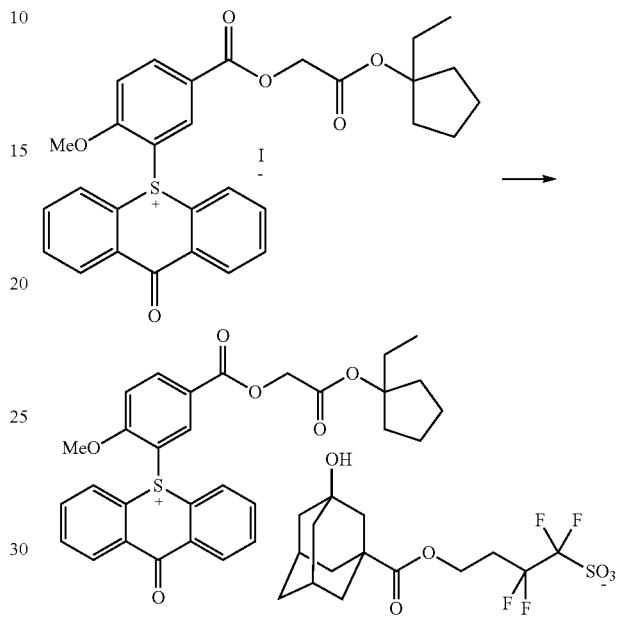

10-(5-((2-(1-ethylcyclopentyloxy)-2-oxoethoxy)carbonyl)-2-methoxyphenyl)-9-oxo-4,4a,9,10-tetrahydrothioxanthylium iodide (5.00 g, 7.73 mmol) and 3-hydroxyadamantane-acetoxy-1,1,2,2-tetrafluorobutane-1-sulfonate sodium salt (3.46 g, 8.12 mmol) were dissolved in dichloromethane (125 mL) and water (125 mL) and stirred at r.t. overnight. The layers were separated and the aqueous phase washed with dichloromethane (3×100 mL). The combined organic layers were washed with water (4×250 mL) and concentrated to afford the title compound (5.56 g, 96%) as a light orange solid. NMR (300 MHz, $(CD_3)_2SO$) δ: 9.04 (vis s, 1H), 8.51-8.59 (m, 2H), 8.39 (dd, J=10, 2.4 Hz, 1H), 8.21-8.27 (m, 2H), 7.92-8.06 (m, 4H), 7.35 (d, J=10 Hz, 1H), 4.91 (s, 2H), 4.57 (s, 1 OH), 4.23 (t, J=6 Hz, 2H), 3.47 (s, 3H), 2.43-2.63 (m, 4H), 1.90-2.12 (m, 7H), 1.44-1.73 (m, 15H), 0.88 (t, J=7 Hz, 3H).

Example 10

Synthesis of 10-(5-carboxy-2-methoxyphenyl)-9-oxo-2-(trifluoromethyl)-4,4a,9,10-tetrahydrothioxanthylium trifluoromethanesulfonate

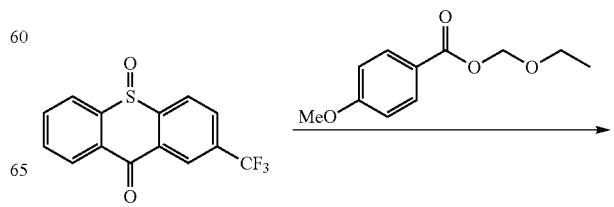

-continued

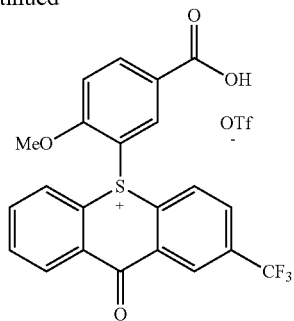

Triflic anhydride (19.8 mL, 117 mmol) was added to a solution of 2-(trifluoromethyl)-thioxanthen-9-one oxide (23.2 g, 78.4 mmol) and ethoxymethyl 4-methoxybenzoate (21.4 g, 102 mmol) in dichloromethane (300 mL) at −78° C. and slowly warmed to 0° C. The reaction mixture was quenched with water (300 mL), stirred overnight and filtered. The solid was refluxed in MTBE (500 mL) and filtered to afford the title compound (5.5 g, 12% (not optimized)) as a white solid. NMR (500 MHz, $(CD_3)_2SO$) δ: 9.06 (s, 1H), 8.73 (vis s, 1H), 8.56-8.59 (m, 1H), 8.48 (d, J=8.5 Hz, 1H), 8.39 (d, J=8.5 Hz, 1H), 8.33-8.36 (m, 1H), 8.20-8.24 (m, 1H), 7.97-8.08 (m, 4H), 7.30 (d, J=9 Hz, 1H), 3.43 (s, 3H).

Example 11

Synthesis of 10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium trifluoromethanesulfonate

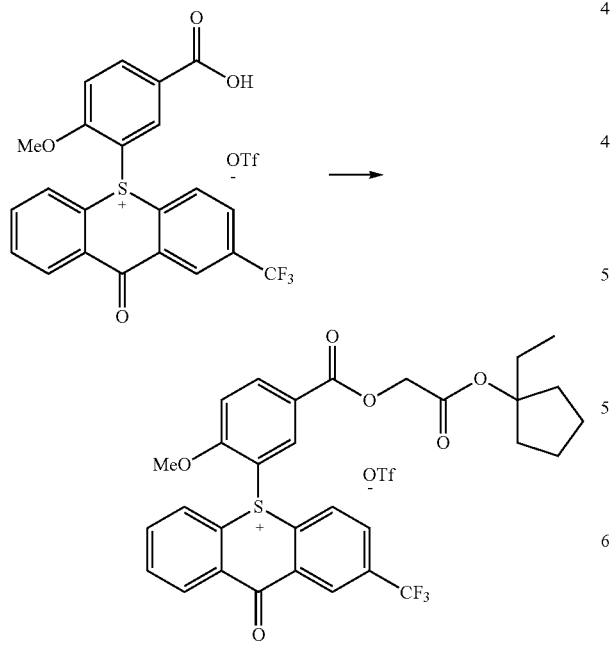

1-ethylcyclopentyl 2-bromoacetate (2.97 g, 12.6 mmol)) was added to a solution of 10-(5-carboxy-2-methoxyphenyl)-9-oxo-2-(trifluoromethyl)-4,4a,9,10-tetrahydrothioxanthylium (6.69 g, 11.5 mmol) and cesium carbonate (5.24 g, 16.1 mmol) in DMF (50 mL) at 0° C. and warmed to r.t. overnight. The reaction muxture was diluted with water (200 mL), extracted with dichloromethane (4×100 mL) and the combined organics washed with dilute HCl (200 mL) then water (2×200 mL). The combined aqueous layers were back extracted with dichloromethane (2×150 mL) and the combined organic layers dried ($Na_2SO_4$), concentrated and purified via silica gel flash column chromatography (step gradient DCM to 9:1 DCM:MeOH) to afford the title compound (5.21 g, 62% (non-optimized)) as an off white solid. NMR (500 MHz, $(CD_3)_2SO$) δ: 9.18 (vis s, 1H), 8.73 (vis s, 1H), 8.57 (d, J=8 Hz, 1H), 8.49 (d, J=8.5 Hz, 1H), 8.37-8.44 (m, 2H), 8.22 (d, J=8 Hz, 1H), 7.98-8.05 (m, 2H), 7.34 (d, J=8 Hz, 1H), 4.92 (s, 2H), 3.43 (s, 3H), 2.00-2.09 (m, 2H), 1.96 (q, J=7.5 Hz, 2H), 1.55-1.73 (m, 6H), 0.89 (t, J=7.5 Hz, 3H).

Example 12

Synthesis of 10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium iodide

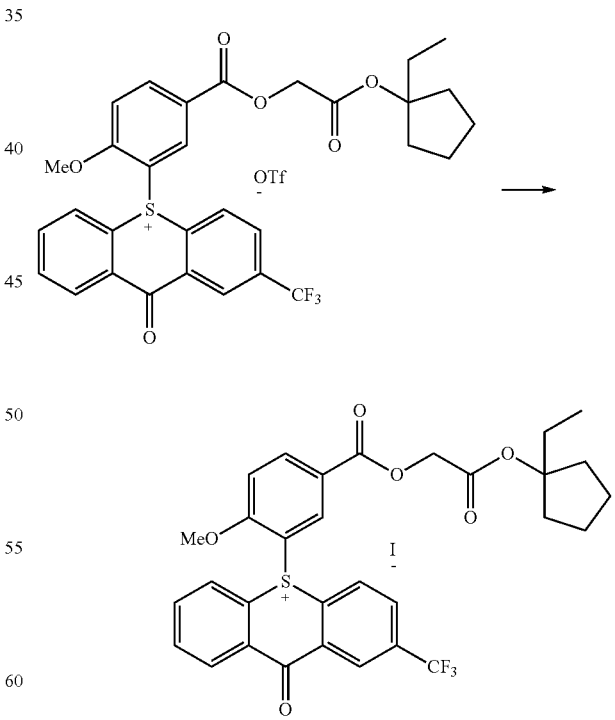

10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium (5.21 g, 7.07 mmol) was dissolved in dichloromethane (100 mL) and washed with 1M aqueous sodium iodide (4×150 mL), water (4×150 mL), dried (Na$_2$SO$_4$) and concentrated to afford the title compound (3.81 g, 75%) as a light orange solid. NMR (500 MHz, (CD$_3$)$_2$SO) δ: 9.17 (vis s, 1H), 8.73 (vis s, 1H), 8.55-8.59 (m, 1H), 8.47-8.52 (m, 1H), 8.37-8.43 (m, 2H), 8.23 (d, J=8.5 Hz, 1H), 7.98-8.07 (m, 2H), 7.35 (d, J=8.5 Hz, 2H).

Example 13

Synthesis of 10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium 3-hydroxyadamantane-acetoxy-1,1,2,2-tetrafluorobutane-1-sulfonate

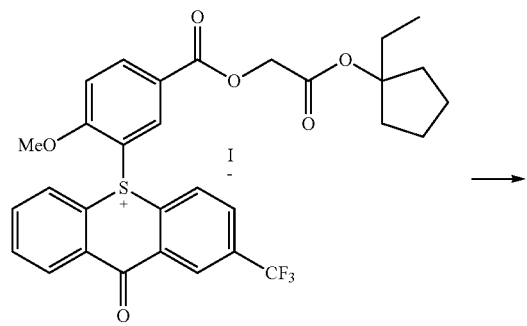

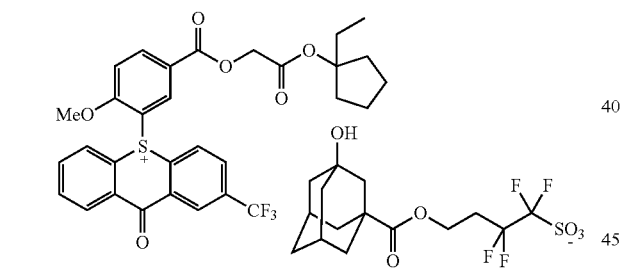

10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium iodide (0.8 g, 1.12 mmol) and 3-hydroxyadamantane-acetoxy-1,1,2,2-tetrafluorobutane-1-sulfonate sodium salt (0.501 g, 1.18 mmol) were dissolved in dichloromethane (25 mL) and water (25 mL) and stirred at r.t. overnight. The layers were separated and the aqueous phase washed with dichloromethane (3×50 mL). The combined organic layers were washed with water (4×50 mL) and concentrated to afford the title compound (1.04 g, 95%) as a light orange solid. NMR (300 MHz, (CD$_3$)$_2$SO) δ: 9.21 (vis s, 1H), 8.73-8.78 (m, 1H), 8.37-8.61 (m, 6H), 8.21-8.26 (m, 1H), 7.97-8.08 (m, 2H), 7.35 (d, J=10 Hz, 1H, 4.94 (s, 2H), 4.24 (t, J=6 Hz, 2H), 3.45 (s, 3H), 2.44-2.63 (m, 4H), 1.89-2.12 (m, 7H), 1.44-1.74 (m, 15H), 0.88 (t, J=7 Hz, 3H).

Example 14

Synthesis of 10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium 1,1-difluoro-2-(methacryloyloxy)ethanesulfonate

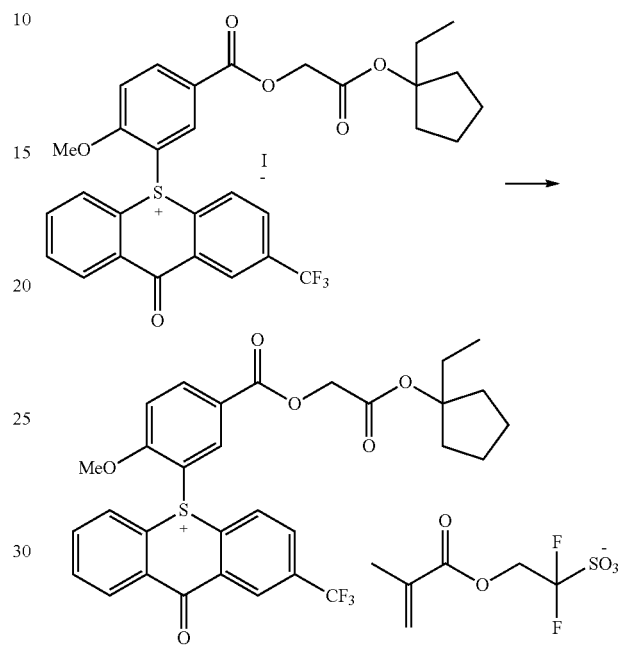

10-(5-((2-(1-ethylcyclopentyloxy)-2-oxoethoxy)carbonyl)-2-methoxyphenyl)-9-oxo-2-(trifluoromethyl)-4,4a,9,10-tetrahydrothioxanthylium iodide (2.93 g, 4.10 mmol) and triethylammonium 1,1-difluoro-2-(methacryloyloxy)ethanesulfonate (1.43 g, 4.31 mmol) were dissolved in dichloromethane (100 mL) and water (100 mL) and stirred at r.t. overnight. The layers were separated and the aqueous phase washed with dichloromethane (3×100 mL). The combined organic layers were washed with water (4×200 mL) and concentrated to afford the title compound (3.23 g, 97%) as a light orange solid. NMR (300 MHz, (CD$_3$)$_2$SO) δ: 9.21 (vis s, 1H), 8.72-8.79 (m, 1H), 8.50-8.64 (m, 2H), 8.37-8.48 (m, 2H), 8.22-8.30 (m, 1H), 7.99-8.09 (m, 2H), 7.36 (d, J=8.7 Hz, 1H), 6.09- 6.12 (m, 1H), 5.76-5.80 (m, 1H), 4.49 (s, 2H), 4.63 (t, J=6H, 2H), 3.46 (s, 3H), 1.90-2.13 (m, 7H), 1.52-1.75 (m, 6H), 0.90 (t, J=7 Hz, 3H).

Example 15

Synthesis of 2-hydroxy-1,3-dimethyl-9H-thioxanthen-9-one

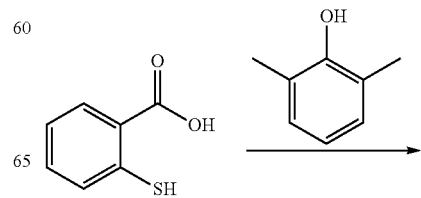

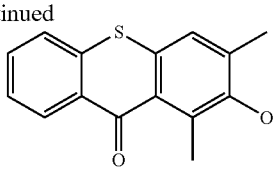

2,6-dimethylphenol (47.5 g, 0.389 mol) was added in portions to a solution of thiosalicylic acid (15.0 g, 97.3 mmol) in sulfuric acid (150 mL) and stirred at r.t. for 2 h. The reaction mixture was poured onto ice water (700 mL), filtered, suspended in dichloromethane (500 mL), washed with saturated sodium carbonate (400 mL), dried ($Na_2SO_4$), concentrated and purified by silica gel flash column chromatography (neutralized with TEA gradient 1:1 heptanes: acetone to 100% acetone) to afford the title compound (13.2 g, 53%) as an off white solid. NMR (300 MHz, $(CD_3)_2SO$) δ: 8.84 (s, 1OH), 8.28 (d, J=8.1 Hz, 1H), 7.62-7.75 (m, 2), 7.49 (t, J=8.1 Hz, 1H), 7.41 (s, 1H), 2.66 (s, 3H), 2.32 (s, 3H).

Example 16

Synthesis of 10-(4-tert-butylphenyl)-2-hydroxy-1,3-dimethyl-9-oxo-9,10-dihydrothioxanthylium 1,1,2,2,3,3,4,4,4-nonafluorobutane-1-sulfonate

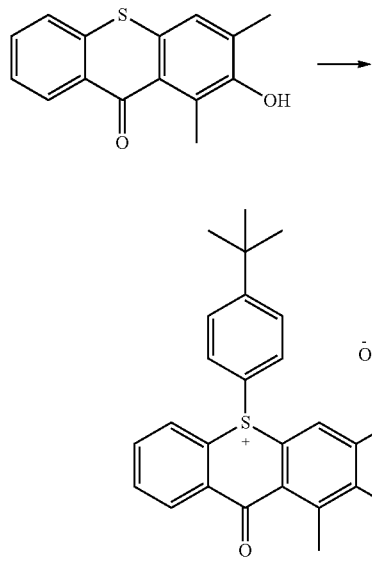

2-hydroxy-1,3-dimethyl-9H-thioxanthen-9-one (0.500 g, 1.95 mmol), bis(4-tert-butylphenyl)iodonium 1,1,2,2,3,3,4,4,4-nonafluorobutane-1-sulfonate (1.55 g, 2.24 mmol) and copper benzoate (0.015 g, 0.045 mmol) were dissolved in chlorobenzene (25 mL), heated to 110° C. for 2 h and cooled to r.t. The reaction mixture was diluted with dichloromethane (150 mL), washed with water (6×150 mL) and concentrated. The crude solid was reflux in MTBE (200 mL) for 1 h, cooled to r.t. and filtered to afford the title compound (1.34 g, 75%) as an off white solid. NMR (500 MHz, $(CD_3)_2SO$) δ: 10.10-10.25 (brs, 1OH), 8.29-8.37 (m, 2H), 8.05 (s, 1H), 7.96-8.25 (m, 2H), 7.64 (d, J=9 Hz, 2H), 7.59 (d, J=9 Hz, 2H), 2.62 (s, 3H), 2.33 (s, 3H), 1.22 (s, 9H).

Example 17

Synthesis of 10-(4-tert-butylphenyl)-2-(2-(1-ethyl-cyclopentyloxy)-2-oxoethoxy)-1,3-dimethyl-9-oxo-9,10-dihydrothioxanthylium

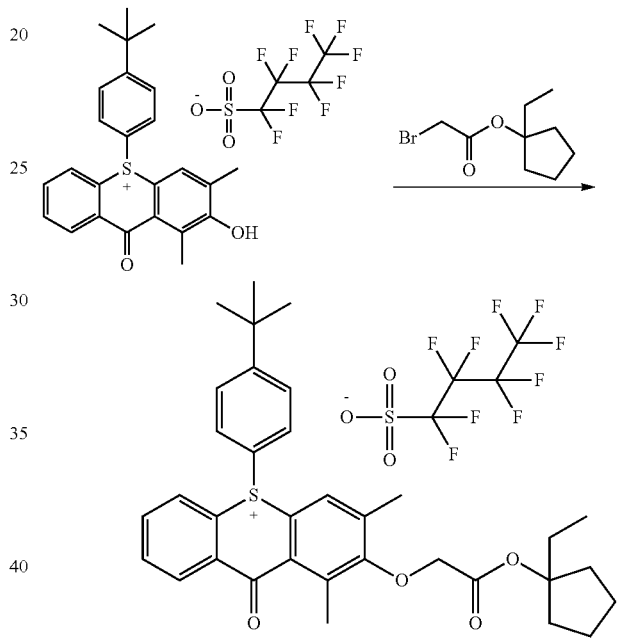

1-ethylcyclopentyl 2-bromoacetate (0.225 g, 0.958 mmol) was added to a solution of 10-(4-tert-butylphenyl)-2-hydroxy-1,3-dimethyl-9-oxo-9,10-dihydrothioxanthylium (0.600 g, 0.871 mmol) and cesium carbonate (0.397 g, 1.22 mmol) in DMF (15 mL) at 0° C., warmed to r.t. and stirred for 24 h. The reaction muxture was diluted with water (40 mL), extracted with dichloromethane (4×30 mL) and the combined organics washed with dilute HCl (50 mL) then water (3×50 mL). The combined aqueous layers were back extracted with dichloromethane (2×40 mL) and the combined organic layers were concentrated and precipitated from MTBE/heptanes to afford the title compound (0.375 g, 51%) as a light brown solid. NMR (500 MHz, $(CD_3)_2CO$) δ: 8.51 (d, J=7.5 Hz, 1H), 8.43 (d, J=7.5 Hz, 1H), 8.31 (s, 1H), 8.13 (t, J=8.0 Hz, 1H), 8.08 (t, J=7.5 Hz, 1H), 7.82 (dd, J=8.5, 1.5 Hz, 2H), 7.73 (dd, J=8.5, 1.5 Hz, 2H), 4.65 (s, 2H), 2.79 (s, 3H), 2.52 (s, 3H), 2.04-2.18 (m, 4H), 1.54-1.77 (m, 6H), 1.28 (s, 9H), 0.88 (t, J=7.0 Hz, 3H). $^{19}F$ NMR (300 MHz, $(CD_3)_2CO$) δ: −82.21 (3F), −115.89 (2F), −122.42 (2F), −127.00 (2F).

Example 18

Synthesis of 5-(5-carboxy-2-methoxyphenyl)-5H-thianthrenoxide-5-ium 1,1,2,2,3,3,4,4,4-nonafluorobutane-1-sulfonate

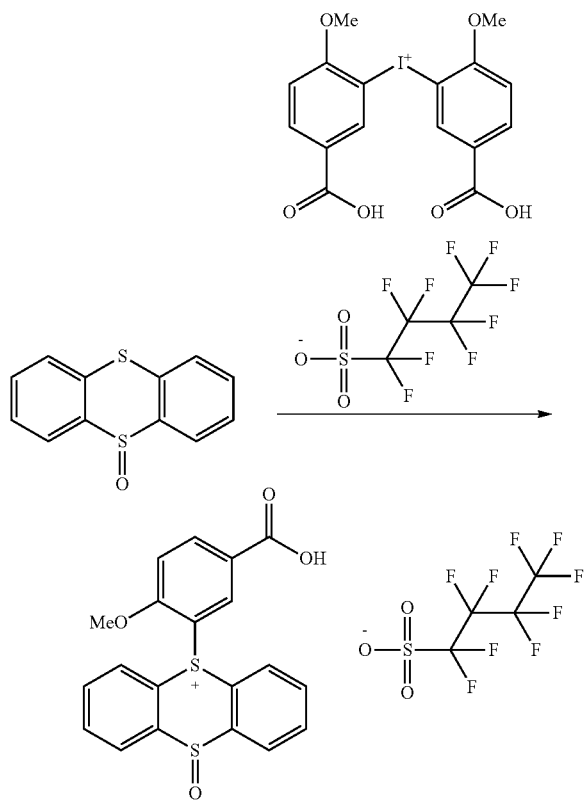

Thianthrene oxide (2.00 g, 8.61 mmol) and bis(5-carboxy-2-methoxyphenyl)iodonium 1,1,2,2,3,3,4,4,4-nonafluorobutane-1-sulfonate (6.27 g, 8.61 mmol) and copper benzoate (0.066 g, 0.215 mmol) are dissolved in chlorobenzene (30 mL) and heated to 120° C. for 2 h and cooled to room temperature. The reaction mixture is diluted with dichloromethane (150 mL), washed with water (6×150 mL), concentrated and precipitated from MTBE/heptanes to afford the title compound (theoretical yield=5.88 g) as a white solid.

Example 19

Synthesis of 5-(5-((2-(1-ethylcyclopentyloxy)-2-oxoethoxy)carbonyl)-2-methoxyphenyl)-5H-thianthrenoxide-5-ium 1,1,2,2,3,3,4,4,4-nonafluorobutane-1-sulfonate

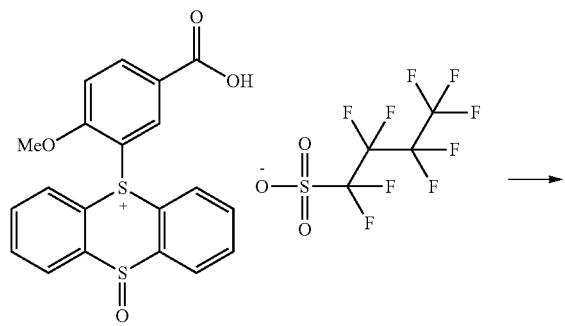

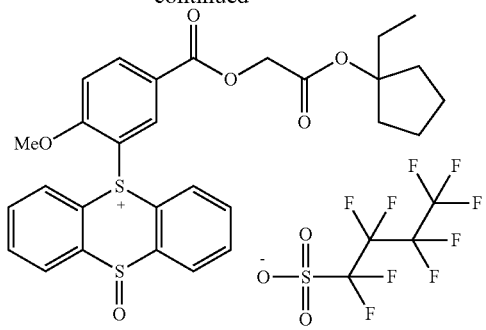

1-ethylcyclopentyl 2-bromoacetate (0.500 g, 2.13 mmol) is added to a solution of 5-(5-carboxy-2-methoxyphenyl)-5H-thianthrenoxide-5-ium 1,1,2,2,3,3,4,4,4-nonafluorobutane-1-sulfonate (1.31 g, 1.91 mmol) and cesium carbonate (0.871 g, 2.67 mmol) in DMF (50 mL) at 0° C., warmed to r.t. and stirred overnight. The reaction muxture is diluted with water (200 mL), extracted with dichloromethane (4×100 mL) and the combined organics washed with dilute HCl (200 mL) then water (3×250 mL). The combined aqueous layers are back extracted with dichloromethane (2×100 mL) and the combined organic layers are concentrated and precipitated from MTBE/heptanes to afford the title compound (theoretical yield=1.61 g) as a white solid.

Example 20

Synthesis of 10-(4-tert-butylphenyl)-2-carboxy-9-oxo-9,10-dihydrothioxanthylium 1,1,2,2,3,3,4,4,4-nonafluorobutane-1-sulfonate

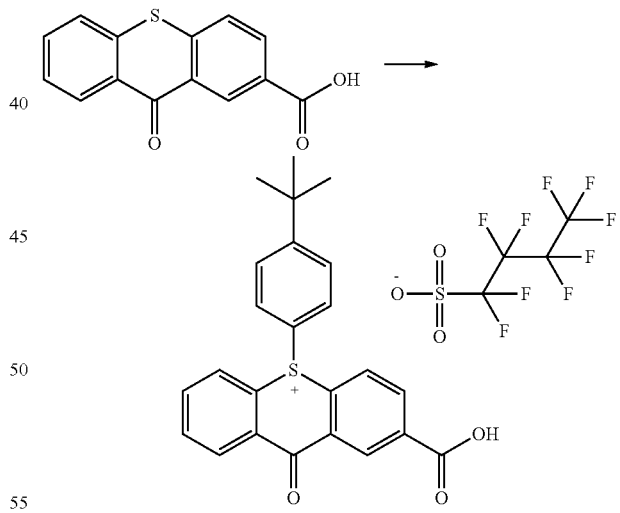

9-oxo-9H-thioxanthene-2-carboxylic acid (prepared as disclosed in *Org. Biomol. Chem.* 2006, 4, 4101.) (1.00 g, 3.91 mmol), bis(4-tert-butylphenyl)iodonium 1,1,2,2,3,3,4,4,4-nonafluorobutane-1-sulfonate (2.70 g, 3.91 mmol) and copper benzoate (0.098 mmol, 0.030 g) are dissolved in chlorobenzene (30 mL) and heated to 120° C. for 2 h and cooled to room temperature. The reaction mixture is diluted with dichloromethane (150 mL), washed with water (6×100 mL), concentrated and precipitated from MTBE/heptanes to afford the title compound (theoretical yield=2.69 g) as a white solid.

Example 21

Synthesis of 10-(4-tert-butylphenyl)-2-((2-(1-ethyl-cyclopentyloxy)-2-oxoethoxy)carbonyl)-9-oxo-9,10-dihydrothioxanthylium 1,1,2,2,3,3,4,4,4-nonafluorobutane-1-sulfonate

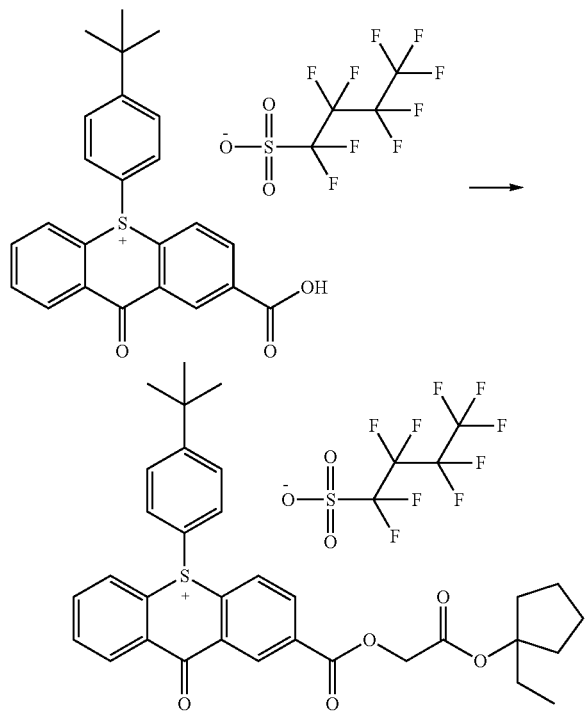

1-ethylcyclopentyl 2-bromoacetate (0.500 g, 2.13 mmol) is added to a solution of 10-(4-tert-butylphenyl)-2-carboxy-9-oxo-9,10-dihydrothioxanthylium 1,1,2,2,3,3,4,4,4-nonafluorobutane-1-sulfonate (1.32 g, 1.91 mmol) and cesium carbonate (0.871 g, 2.67 mmol) in DMF (50 mL) at 0° C., warmed to r.t. and stirred overnight. The reaction muxture is diluted with water (200 mL), extracted with dichloromethane (4×100 mL) and the combined organics washed with dilute HCl (200 mL) then water (3×250 mL). The combined aqueous layers are back extracted with dichloromethane (2×100 mL) and the combined organic layers are concentrated and precipitated from MTBE/heptanes to afford the title compound (theoretical yield=1.61 g) as a white solid.

Example 22

Preparation of Polymer

Heel solution was made by dissolving 2-phenylpropan-2-yl methacrylate (0.39 g), 2-oxotetrahydrofuran-3-yl methacrylate (0.33 g), 3,5-bis(1,1,1,3,3,3-hexafluoro-2-hydroxypropan-2-yl)cyclohexyl methacrylate (0.57 g) and 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate (0.31 g) in 12.81 g acetonitrile/THF (2/1 v/v). Feed solution was prepared by dissolving 2-phenylpropan-2-yl methacrylate (185.54 g, 0.967 mol), 2-oxotetrahydrofuran-3-yl methacrylate (204.27, 1.26 mol), 3,5-bis(1,1,1,3,3,3-hexafluoro-2-hydroxypropan-2-yl)cyclohexyl methacrylate (127.98 g, 0.29 mol) and 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate (81.5 g, 0.132 mol) in 606 g EL/GBL (30/70 v/v). Initiator solution was prepared by dissolving 65.96 g initiator (V-65) in 66 g acetonitrile/THF (2/1 v/v), The polymerization was carried out in a 2 L 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pump over a 4 hour time period. The contents were then let to stir for additional 2 hours, whereby, the reaction was quenched using hydroquinone (2.0 g). The contents were cooled to room temperature and precipitated twice out of 10× (by weight) IPE/MeOH 95/5 (w/w). The polymer obtained was dried in vacuuo after each precipitation step at 50° C. for 24 hours to yield 500 g polymer.

Example 23

Preparation and Processing of Photoresist Composition

A positive-tone photoresist composition was prepared by combining 4.943 g of 10 wt % solution in ethyl lactate of a polymer of Example 22, 9.627 g of 2 wt % solution in ethyl lactate of Example 9, 6.525 g of 0.5 wt % solution in ethyl lactate 1,1',1'',1'''-(ethane-1,2-diylbis(azanetriyl))tetrapropan-2-ol, 0.099 g of a 0.5 wt % solution in ethyl lactate of fluorinated surfactant (Omnova PF656), 0.021 g of ethyl lactate and 8.784 g of methyl-2-hydroxyisobutyrate (HBM).

The formulated resist was passed through a 0.01 µm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with 0.26N aqueous tetramethylammonium hydroxide.

The following results were obtained with this photoresist: Esize (exposure dose (mJ/cm$^2$) required to provide a 1:1 resolution at the top and bottom of a 30 nm contact hole pattern) 30 nm CH) 27.73 mJ/cm$^2$; CDU (critical dimension uniformity) 1.97 nm.

Example 24

Preparation and Processing of Photoresist Composition

A positive-tone photoresist composition was prepared by combining 4.943 g of a 10 wt % solution in ethyl lactate of the polymer in example 22, 9.430 g of a 2 wt % solution in ethyl lactate of example 13, 6.525 g of a 0.5 wt % solution in ethyl lactate of 1,1',1'',1'''-(ethane-1,2-diylbis(azanetriyl)) tetrapropan-2-ol, 0.099 g of a 0.5 wt % solution in ethyl lactate of fluorinated surfactant (Omnova PF656), 0.021 g of ethyl lactate and 8.784 g of HBM.

The formulated resist was passed through a 0.01 µm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with 0.26N aqueous tetramethylammonium hydroxide.

Example 25

Comparative

A comparative photoresist (Comparative Photoresist in below Table 1) was prepared and processed as described in Example 23 above, but where the acid generator compound contain a fused 5-membered sulfonium ring (i.e. fused $(C)_4S+$ ring) in place of the fused thioxanthone ring.

The following results were obtained for this comparative photoresist: Esize ((exposure dose (mJ/cm$^2$) 30 nm CH)=35.68 mJ/cm$^2$; CDU (critical dimension uniformity) 2.04 nm. Thus, the use of the acid generator compound of Example 9, as formulated in example 23 provided 22% improved photospeed (Esize) and 3% improved CDU.

TABLE 1

Photospeed Results

| Example | E0 (mJ/cm$^2$) |
|---|---|
| Photoresist of Example 23 | 1.8 |
| Photoresist of Example 24 | 0.8 |
| Comparative Photoresist | 4.4 |

Example 26

Reduction Potential Analyses

Reduction potential were determined by the standard electrochemical potential assay, as that assay is defined herein. The following values were determined (all values vs. Ag/AgCl, cathodic peak potential):

For the cations produced in each of above Examples 6, 7, 8, 9 and 19: −0.66 volts. For the cations produced in each of above Examples 11, 12, 13 and 14: −0.61 V. As a comparative analysis, for triphenyl sulfonium cation: −1.44 V.

What is claimed is:

1. A photoresist composition comprising:
   (a) a polymer; and
   (b) an acid generator comprising:
      (i) a thioxanthone moiety; and
      (ii) one or more covalently linked acid labile-groups,
   wherein the acid generator exhibits a reduction potential of −0.9 to 0 V (vs. Ag/AgCl, cathodic peak potential) in a standard reduction potential assay.

2. The photoresist composition of claim 1 wherein the acid generator comprises an acid-labile group of the following Formula (II):

—(C=O)OR$^3$    (II)

wherein R3 is a non-hydrogen substituent that provides an acid-labile moiety.

3. The photoresist composition of claim 1 wherein the acid generator comprises an acid-labile group of the following Formula (III):

—O(CXY)$_n$R$^3$    (III)

wherein X and Y are independently hydrogen or a non-hydrogen substituent; R$^3$ is a non-hydrogen substituent that provides an acid-labile moiety; and n is a positive integer.

4. The photoresist composition of claim 1 wherein the acid generator is covalently bound to a polymer.

5. A method for providing a photoresist relief image, comprising:
   a) applying a coating layer of a photoresist composition of claim 1 on a substrate; and
   b) exposing the photoresist composition layer to activating radiation and developing the exposed photoresist composition coating layer.

6. The method of claim 5 wherein the photoresist composition layer is exposed to EUV or e-beam radiation.

7. The photoresist composition of claim 1 wherein the cleavage product of the one or more covalently linked acid labile-groups comprises a carboalicyclic group.

8. The photoresist composition of claim 1 wherein the cleavage product of the one or more covalently acid labile-groups comprises an optionally substituted adamantyl group.

9. The photoresist composition of claim 1 wherein the cleavage product of the one or more covalently linked acid labile-groups comprises an optionally substituted cyclopentyl, cyclohexyl or cycloheptyl group.

10. The photoresist composition of claim 1 wherein the cleavage product of the one or more covalently linked acid labile-groups comprises a heteroalicyclic group.

11. The photoresist composition of claim 1 wherein the cleavage product of the one or more covalently linked acid labile-groups comprises an aromatic group.

12. The photoresist composition of claim 11 wherein the cleavage product of the one or more covalently linked acid labile-groups comprises an optionally substituted phenyl or naphthyl.

13. An acid generator comprising:
   (i) a thioxanthone moiety; and
   (ii) one or more covalently linked acid labile-groups,
   wherein the acid generator exhibits a reduction potential of −0.9 to 0 V (vs. Ag/AgCl, cathodic peak potential) in a standard reduction potential assay.

14. A photoresist composition comprising:
   (a) a polymer; and
   (b) an acid generator compound that comprises a structure of Formula (I):

(I)

[chemical structure showing thioxanthone with S+ bearing R, substituents (T)$_m$ and (T')$_{m'}$, X bridging, (L)$_n$ and (L')$_{n'}$, with counter anion Z$^-$]

wherein: Z is a counter anion;
   R is a non-hydrogen substituent;
   X is >C=O;
   each T and each T' are the same or different non-hydrogen substituent;
   each L and each L' are the same or different acid-labile group, with T, L, T', and U nonhydrogen groups may be taken together to form a ring;
   m and m' are each independently 0, 1, 3 or 4; and
   n and n' are each independently 0, 1, 2, 3 or 4,
   wherein if R does not comprise an acid-labile group, then at least one of n and n' is greater than zero whereby the acid generator compound comprises at least one acid-labile group; and
   wherein the acid generator compound exhibits a reduction potential of −0.9 to 0 V (vs. Ag/AgCl, cathodic peak potential) in a standard reduction potential assay.

15. The photoresist composition of claim 14 wherein the acid generator comprises a structure of Formula (IA):

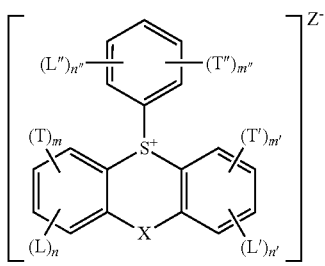

wherein: Z is a counter anion;
X is >C=O;
each T, each T' and each T" are the same or different non-hydrogen substituent;
each L, each L' and each L" are the same or different acid-labile group, with T, L, T', L', T" and L" non-hydrogen groups may be taken together to form a ring;
m and m' are each independently 0, 1, 2, 3 or 4; m" is 0, 1, 2, 3, 4 or 5; n and n' are each independently 0, 1, 2, 3 or 4; n" is independently 0, 1, 2, 3, 4 or 5; and at least one of n, n' and n" are other than 0.

16. The photoresist composition of claim 14 wherein the acid generator comprises a structure of Formula (IC):

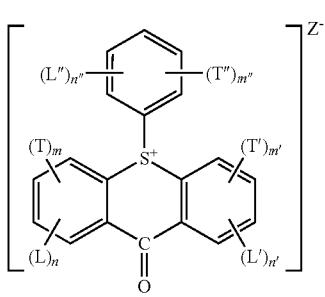

wherein: Z is a counter anion;
each T, each T' and each T" are the same or different non-hydrogen substituent;
each L, each L' and each L" are the same or different acid-labile group, with T, L, T', L', T" and L" non-hydrogen groups may be taken together to form a ring;
m and m' are each independently 0, 1, 2, 3 or 4; m" is 0, 1, 2, 3, 4 or 5; n and n' are each independently 0, 1, 2, 3 or 4; n" is independently 0, 1, 2, 3, 4 or 5; and at least one of n, n' and n" are other than 0.

17. The photoresist composition of claim 14 wherein the acid generator comprises an acid-labile group of the following Formula (II):

—(C═O)OR$^3$      (II)

wherein R$^3$ is a non-hydrogen substituent that provides an acid-labile moiety.

18. The photoresist composition of claim 14 wherein the acid generator comprises an acid-labile group of the following Formula (III):

—O(CXY)$_n$R$^3$      (III)

wherein X and Y are independently hydrogen or a non-hydrogen substituent; R$^3$ is a non-hydrogen substituent that provides an acid-labile moiety; and n is a positive integer.

19. The photoresist composition of claim 14 wherein the acid generator compound is covalently bound to a polymer.

20. The photoresist composition of claim 14 wherein the cleavage product of the one or more acid labile-groups comprises a carboalicyclic group.

21. The photoresist composition of claim 20 wherein the cleavage product of the one or more acid labile-groups comprises an optionally substituted adamantyl group.

22. The photoresist composition of claim 20 wherein the cleavage product of the one or more acid labile-groups comprises an optionally substituted cyclopentyl, cyclohexyl or cycloheptyl group.

23. The photoresist composition of claim 14 wherein the cleavage product of the one or more acid labile-groups comprises a heteroalicyclic group.

24. The photoresist composition of claim 14 wherein the cleavage product of the one or more acid labile-groups comprises an aromatic group.

25. The photoresist composition of claim 24 wherein the cleavage product of the one or more acid labile-groups comprises an optionally substituted phenyl or naphthyl.

26. The photoresist composition of claim 14 wherein the acid generator comprises a cation component selected from the following:

10-(5-((2-1(ethylcyclopentyloxy)-2-oxoethoxy)carbonyl)-2-methoxyphenyl)-9-oxo-4,4a,9,10-tetrahydrothioxanthylium;

10-(5-((2-1(ethylcyclopentyloxy)-2-oxoethoxy)carbonyl)-2-methoxyphenyl)-9-oxo-2-(trifluoromethyl)-4,4a,9,10-tetrahydrothioxanthylium;

10-(4-tert-butylphenyl)-2-(2-1(ethylcyclopentyloxy)-2-oxoethoxy)-1,3-dimethyl-9-oxo-9,10-dihydrothioxanthylium; and 10-(4-tert-butylphenyl)2-(2-1(ethylcyclopentyloxy)-2-oxoethoxy)carbonyl)-9-oxo-9,10-dihydrothioxanylium.

27. The photoresist composition of claim 14 wherein the acid generator comprises a cation component selected from the following:

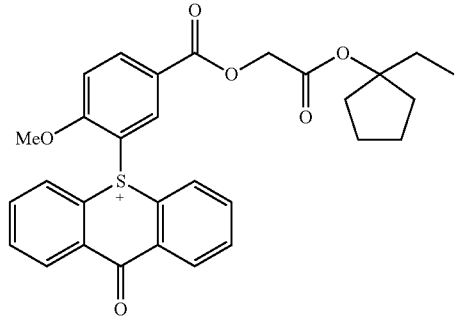

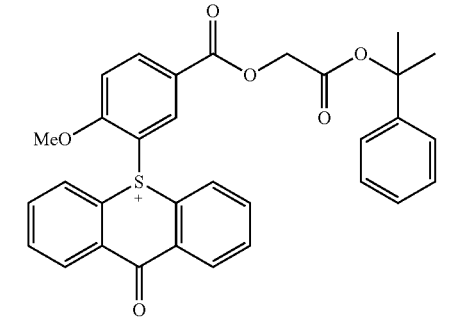

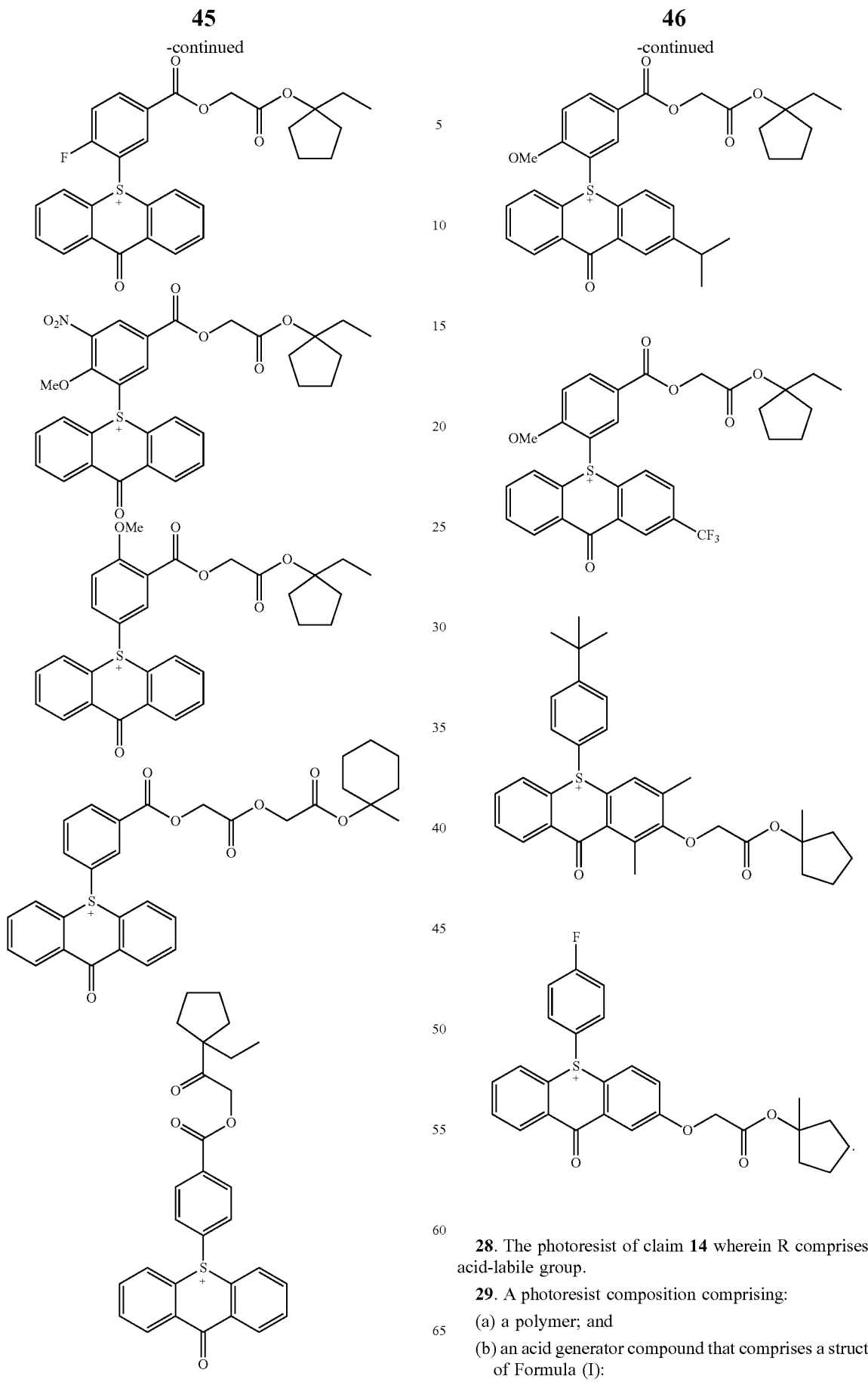
28. The photoresist of claim 14 wherein R comprises an acid-labile group.
29. A photoresist composition comprising:
(a) a polymer; and
(b) an acid generator compound that comprises a structure of Formula (I):

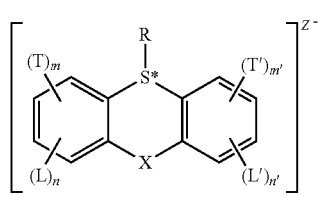 (I)

wherein: Z is a counter anion;
R is a non-hydrogen substituent;
X is >C=O;
each T and each T' are the same or different non-hydrogen substituent;
each L and each L' are the same or different acid-labile group, with T, L, T', and L' nonhydrogen groups may be taken together to form a ring;
m and m' are each independently 0, 1, 2, 3 or 4; and
n and n' are each independently 0, 1, 2, 3 or 4,
wherein if R does not comprise an acid-labile group, then at least one of n and n' is greater than zero whereby the acid generator compound comprises at least one acid-labile group; and
wherein the cleavage product of the one or more covalently linked acid labile-groups comprises a heteroalicyclic group.

* * * * *